(12) United States Patent
Anderson

(10) Patent No.: US 8,989,972 B2
(45) Date of Patent: Mar. 24, 2015

(54) LEADER-FOLLOWER FULLY-AUTONOMOUS VEHICLE WITH OPERATOR ON SIDE

(71) Applicant: Deere & Company, Moline, IL (US)

(72) Inventor: Noel Wayne Anderson, Fargo, ND (US)

(73) Assignee: Deere & Company, Moline, IL (US)

( * ) Notice: Subject to any disclaimer, the term of this patent is extended or adjusted under 35 U.S.C. 154(b) by 272 days.

(21) Appl. No.: 13/677,532

(22) Filed: Nov. 15, 2012

(65) Prior Publication Data

US 2015/0025708 A1 Jan. 22, 2015

Related U.S. Application Data

(63) Continuation-in-part of application No. 12/329,930, filed on Dec. 8, 2008, which is a continuation-in-part of application No. 12/208,752, filed on Sep. 11, 2008, now Pat. No. 8,392,065, which is a continuation-in-part of application No. 12/208,659, filed on Sep. 11, 2008, now Pat. No. 8,229,618, which is a continuation-in-part of application No. 12/208,691, filed on Sep. 11, 2008, now Pat. No. 8,818,567, which is a continuation-in-part of application No. 12/208,851, filed on Sep. 11, 2008, which is a continuation-in-part of application No. 12/208,885, filed on Sep. 11, 2008, now Pat. No. 8,195,358, which is a continuation-in-part of application No. 12/208,710, filed on Sep. 11, 2008, now Pat. No. 8,478,493.

(51) Int. Cl.
*G01C 22/00* (2006.01)
*G05D 1/00* (2006.01)
(Continued)

(52) U.S. Cl.
CPC .............. *G05D 1/0231* (2013.01); *A41D 1/002* (2013.01); *A61B 5/02055* (2013.01); *A61B 5/021* (2013.01); *A61B 5/02438* (2013.01); *A61B 5/1112* (2013.01); *A61B 5/145* (2013.01); *A61B 5/6804* (2013.01); *A61B 2503/22* (2013.01); *A61B 2562/08* (2013.01); *B60Q 1/26* (2013.01); *B60Q 5/001* (2013.01); *G01S 5/0257* (2013.01); *G01S 13/86* (2013.01); *G01S 13/862* (2013.01); *G01S 13/865* (2013.01); *G01S 13/867* (2013.01); *G01S 19/48* (2013.01); *G05D 1/0033* (2013.01); *G05D 1/021* (2013.01); *G05D 2201/0201* (2013.01); *G05D 2201/0209* (2013.01); *G08C 17/02* (2013.01); *G08C 2201/32* (2013.01); *G08C 2201/51* (2013.01); *H04Q 9/00* (2013.01);
(Continued)

(58) Field of Classification Search
USPC ............ 701/1, 23, 51, 53, 301, 408; 700/253, 700/245, 255
See application file for complete search history.

(56) References Cited

U.S. PATENT DOCUMENTS 4,166,349 A 9/1979 Coenenberg et al.
5,334,986 A 8/1994 Fernhout
(Continued)

FOREIGN PATENT DOCUMENTS

CA 2305606 A1 10/2000
DE 102006017540 A1 10/2007
(Continued)

OTHER PUBLICATIONS

Extended European Search Report, dated Apr. 10, 2014, regarding Application No. EP09176819.2, 8 pages.
(Continued)

*Primary Examiner* — Ronnie Mancho
(74) *Attorney, Agent, or Firm* — Yee & Associates, P.C.

(57) ABSTRACT

The illustrative embodiments provide a method and apparatus for controlling movement of a vehicle. Movement of an operator located at a side of the vehicle is identified with a plurality of sensors located in the vehicle and the vehicle is moved in a path that maintains the operator at the side of the vehicle while the operator is moving.

29 Claims, 13 Drawing Sheets

(51) Int. Cl.
*A61B 5/0205* (2006.01)
*A61B 5/024* (2006.01)
*A61B 5/11* (2006.01)
*A61B 5/00* (2006.01)
*B60Q 1/26* (2006.01)
*B60Q 5/00* (2006.01)
*G05D 1/02* (2006.01)
*G08C 17/02* (2006.01)
*H04Q 9/00* (2006.01)
*H04R 5/02* (2006.01)
*A41D 1/00* (2006.01)
*A61B 5/021* (2006.01)
*A61B 5/145* (2006.01)
*G01S 5/02* (2010.01)
*G01S 13/86* (2006.01)
*G01S 19/48* (2010.01)

(52) U.S. Cl.
CPC ........ *H04Q2209/43* (2013.01); *H04Q 2209/47* (2013.01); *H04R 5/023* (2013.01)
USPC ................ 701/51; 701/53; 701/301; 701/408

(56) References Cited

U.S. PATENT DOCUMENTS

| | | | |
|---|---|---|---|
| 5,416,310 A | 5/1995 | Little | |
| 5,572,401 A | 11/1996 | Carroll | |
| 5,615,116 A * | 3/1997 | Gudat et al. | 701/23 |
| 5,632,044 A | 5/1997 | Sloot | |
| 5,684,476 A | 11/1997 | Anderson | |
| 5,684,696 A * | 11/1997 | Rao et al. | 701/25 |
| 5,734,932 A | 3/1998 | Washisu | |
| 5,892,445 A | 4/1999 | Tomich | |
| 5,911,669 A | 6/1999 | Stentz et al. | |
| 6,032,097 A | 2/2000 | Iihoshi et al. | |
| 6,038,502 A | 3/2000 | Sudo | |
| 6,101,795 A | 8/2000 | Diekhans | |
| 6,108,197 A | 8/2000 | Janik | |
| 6,128,559 A | 10/2000 | Saitou et al. | |
| 6,163,277 A | 12/2000 | Gehlot | |
| 6,191,813 B1 | 2/2001 | Fujisaki et al. | |
| 6,246,932 B1 | 6/2001 | Kageyama et al. | |
| 6,275,283 B1 | 8/2001 | Hasson | |
| 6,313,454 B1 | 11/2001 | Bos et al. | |
| 6,324,586 B1 | 11/2001 | Johnson | |
| 6,356,820 B1 | 3/2002 | Hashimoto et al. | |
| 6,434,622 B1 | 8/2002 | Monteiro et al. | |
| 6,457,024 B1 | 9/2002 | Felsentein et al. | |
| 6,507,486 B2 | 1/2003 | Peterson, III | |
| 6,529,372 B1 | 3/2003 | Ng et al. | |
| 6,552,661 B1 | 4/2003 | Lastinger et al. | |
| 6,581,571 B2 | 6/2003 | Kubesh et al. | |
| 6,584,390 B2 | 6/2003 | Beck | |
| 6,615,570 B2 | 9/2003 | Beck et al. | |
| 6,650,242 B2 | 11/2003 | Clerk et al. | |
| 6,678,580 B2 | 1/2004 | Benneweis | |
| 6,694,260 B1 | 2/2004 | Rekow | |
| 6,708,080 B2 | 3/2004 | Benneweis | |
| 6,728,608 B2 | 4/2004 | Ollis et al. | |
| 6,732,024 B2 | 5/2004 | Rekow et al. | |
| 6,760,654 B2 | 7/2004 | Beck | |
| 6,839,127 B1 | 1/2005 | Anderson | |
| 6,859,729 B2 | 2/2005 | Breakfield et al. | |
| 6,882,897 B1 | 4/2005 | Fernandez | |
| 6,898,501 B2 | 5/2005 | Schubert | |
| 6,917,300 B2 | 7/2005 | Allen | |
| 6,943,824 B2 | 9/2005 | Alexia et al. | |
| 7,064,810 B2 | 6/2006 | Anderson et al. | |
| 7,088,252 B2 | 8/2006 | Weekes | |
| 7,164,118 B2 | 1/2007 | Anderson et al. | |
| 7,167,797 B2 | 1/2007 | Faivre et al. | |
| 7,222,004 B2 | 5/2007 | Anderson | |
| 7,265,970 B2 | 9/2007 | Jordan | |
| 7,266,477 B2 | 9/2007 | Foessel | |
| 7,286,934 B2 | 10/2007 | Gaegauf et al. | |
| 7,299,056 B2 | 11/2007 | Anderson | |
| 7,299,057 B2 | 11/2007 | Anderson | |
| 7,313,404 B2 | 12/2007 | Anderson | |
| 7,317,977 B2 | 1/2008 | Matrosov | |
| 7,317,988 B2 | 1/2008 | Johnson | |
| 7,330,117 B2 | 2/2008 | Ferguson et al. | |
| 7,375,627 B2 * | 5/2008 | Johnson et al. | 340/468 |
| 7,382,274 B1 | 6/2008 | Kermani et al. | |
| 7,400,976 B2 | 7/2008 | Young et al. | |
| 7,474,945 B2 | 1/2009 | Matsunaga | |
| 7,499,776 B2 | 3/2009 | Allard et al. | |
| 7,545,286 B2 | 6/2009 | Yanase | |
| 7,561,948 B2 | 7/2009 | Gaegauf et al. | |
| 7,579,939 B2 | 8/2009 | Schofield et al. | |
| 7,610,125 B2 | 10/2009 | Fitzner et al. | |
| 7,623,951 B2 | 11/2009 | Congdon et al. | |
| 7,668,621 B2 | 2/2010 | Bruemmer | |
| 7,693,624 B2 | 4/2010 | Duggan et al. | |
| 7,719,410 B2 | 5/2010 | Labuhn et al. | |
| 7,725,261 B2 | 5/2010 | Sekiguchi | |
| 7,734,419 B2 | 6/2010 | Kondoh | |
| 7,742,864 B2 | 6/2010 | Sekiguchi | |
| 7,751,945 B2 | 7/2010 | Obata | |
| 7,818,090 B2 | 10/2010 | Okamoto | |
| 7,852,233 B2 | 12/2010 | Cemper | |
| 7,894,982 B2 | 2/2011 | Reeser et al. | |
| 7,899,584 B2 | 3/2011 | Schricker | |
| 7,916,898 B2 | 3/2011 | Anderson | |
| 7,930,056 B2 | 4/2011 | Fernandez | |
| 8,020,657 B2 | 9/2011 | Allard et al. | |
| 8,031,085 B1 | 10/2011 | Anderson | |
| 8,072,309 B2 | 12/2011 | Kraimer et al. | |
| 8,108,098 B2 | 1/2012 | Childress et al. | |
| 8,131,432 B2 | 3/2012 | Seneff et al. | |
| 8,139,108 B2 | 3/2012 | Stratton et al. | |
| 8,140,658 B1 | 3/2012 | Gelvin et al. | |
| 8,175,785 B2 | 5/2012 | Turski et al. | |
| 8,190,331 B2 | 5/2012 | Browne et al. | |
| 8,195,342 B2 | 6/2012 | Anderson | |
| 8,195,358 B2 | 6/2012 | Anderson | |
| 8,200,428 B2 | 6/2012 | Anderson | |
| 8,205,849 B2 | 6/2012 | Shimizu | |
| 8,224,500 B2 | 7/2012 | Anderson | |
| 8,229,618 B2 | 7/2012 | Tolstedt et al. | |
| 8,253,586 B1 | 8/2012 | Matak | |
| 8,255,144 B2 | 8/2012 | Breed et al. | |
| 2001/0045978 A1 | 11/2001 | McConnell et al. | |
| 2002/0059320 A1 | 5/2002 | Tamaru | |
| 2002/0156556 A1 | 10/2002 | Ruffner | |
| 2003/0186712 A1 | 10/2003 | Tillotson | |
| 2004/0078137 A1 * | 4/2004 | Breakfield et al. | 701/200 |
| 2005/0088643 A1 | 4/2005 | Anderson | |
| 2005/0275542 A1 | 12/2005 | Weekes | |
| 2006/0106496 A1 * | 5/2006 | Okamoto | 700/253 |
| 2006/0173593 A1 | 8/2006 | Anderson | |
| 2006/0180647 A1 | 8/2006 | Hansen | |
| 2006/0189324 A1 | 8/2006 | Anderson | |
| 2006/0221328 A1 * | 10/2006 | Rouly | 356/139.04 |
| 2007/0129869 A1 | 6/2007 | Gudat et al. | |
| 2007/0168090 A1 | 7/2007 | DeMarco et al. | |
| 2007/0171037 A1 | 7/2007 | Schofield et al. | |
| 2007/0193798 A1 | 8/2007 | Allard et al. | |
| 2007/0198144 A1 | 8/2007 | Norris et al. | |
| 2008/0009970 A1 * | 1/2008 | Bruemmer | 700/245 |
| 2008/0129445 A1 | 6/2008 | Kraimer et al. | |
| 2008/0167781 A1 | 7/2008 | Labuhn et al. | |
| 2009/0018712 A1 | 1/2009 | Duncan et al. | |
| 2009/0079839 A1 | 3/2009 | Fischer et al. | |
| 2009/0216406 A1 | 8/2009 | Seneff et al. | |
| 2009/0221328 A1 | 9/2009 | Schumacher et al. | |
| 2009/0259399 A1 | 10/2009 | Kotejoshyer et al. | |
| 2009/0266946 A1 | 10/2009 | Shimizu | |
| 2009/0268946 A1 | 10/2009 | Zhang et al. | |
| 2009/0299581 A1 | 12/2009 | Price | |
| 2010/0036546 A1 | 2/2010 | Gomes et al. | |
| 2010/0042297 A1 | 2/2010 | Foster et al. | |
| 2010/0063626 A1 | 3/2010 | Anderson | |

(56) References Cited

U.S. PATENT DOCUMENTS

| | | |
|---|---|---|
| 2010/0063648 A1 | 3/2010 | Anderson |
| 2010/0063651 A1 | 3/2010 | Anderson |
| 2010/0063652 A1 | 3/2010 | Anderson |
| 2010/0063663 A1 | 3/2010 | Tolstedt et al. |
| 2010/0063664 A1 | 3/2010 | Anderson |
| 2010/0063672 A1 | 3/2010 | Anderson |
| 2010/0063673 A1 | 3/2010 | Anderson |
| 2010/0063680 A1 | 3/2010 | Tolstedt et al. |
| 2010/0063954 A1 | 3/2010 | Anderson |
| 2010/0081411 A1 | 4/2010 | Montenero |
| 2010/0131122 A1 | 5/2010 | Dersjo et al. |
| 2010/0179691 A1 | 7/2010 | Gal et al. |
| 2010/0289662 A1 | 11/2010 | Dasilva et al. |
| 2010/0332061 A1 | 12/2010 | Forslow et al. |
| 2011/0021231 A1 | 1/2011 | Burns et al. |
| 2011/0254708 A1 | 10/2011 | Anderson |
| 2012/0029761 A1 | 2/2012 | Anderson |
| 2012/0095651 A1 | 4/2012 | Anderson |
| 2012/0221172 A1 | 8/2012 | Anderson |
| 2012/0277932 A1 | 11/2012 | Anderson |
| 2013/0282200 A1 | 10/2013 | Anderson |

FOREIGN PATENT DOCUMENTS

| | | |
|---|---|---|
| JP | 7159285 A | 6/1995 |
| WO | WO2007051972 A1 | 5/2007 |
| WO | WO2008133394 A1 | 11/2008 |

OTHER PUBLICATIONS

Zappi et al., "Activity recognition from on-body sensors by classifier fusion: sensor scalability and robustness," Proceedings of the 3rd International Conference on Intelligent Sensors, Sensor Networks and Information (ISSNIP 2007), Dec. 2007, pp. 281-286.

"Essay—Video Production," Capitalist Lion.com, http://capitalistlion.com/essay/vid-platforms.html, published as early as Jan. 2003, retrieved on Oct. 13, 2009, 7 pages.

"Submarine Periscopes and Approach Techniques," FleetSubmarine.com, http://fleetsubmarine.com/periscope.html, published as early as Jan. 2002, retrieved on Oct. 13, 2009, 14 pages.

"Video Stabilization," http://www.cfar.umd.edu/~yao/video_stabilization.html, retrieved Oct. 13, 2009, 2 pages.

Borenstein et al., "Where am I? Sensors and Methods for Mobile Robot Positioning," University of Michigan, Ann Arbor, Michigan, Apr. 1996, pp. 1-281.

Deans et al., "Localization and Mapping Using Bearings Only Sensors," http://www.cs.cmu.edu/~rll/guide2001/deans/html/deans.html, published as early as Jan. 1993, retrieved on Oct. 13, 2009, 3 pages.

Hagras et al., "Online Learning of the Sensors Fuzzy Membership Functions in Autonomous Mobile Robots," Proceedings of the 2000 IEEE International Conference on Robotics and Automation, San Francisco, California, pp. 3233-3238, Apr. 2000.

Kelly, "Precision Dilution in Triangulation Based Mobile Robot Position Estimation," Intelligent Autonomous Systems, University of Amsterdam, Amsterdam, The Netherlands, pp. 1-8, 2003.

Kiriy, "A Localization System for Autonomous Golf Course Mowers," Masters Thesis, McGill University, Montreal, Canada, Nov. 2002, 122 pages.

Najjaran et al., "Online Map Building for Terrain Scanning Robots Using a Hybrid Neurofuzzy Kalman Filter," IEEE, 2:814-819, Jun. 2004.

Stella et al., "Self-Location of a Mobile Robot with Uncertainty by Cooperation of a Heading Sensor and a CCD TV Camera," Proceedings of the 13th International Conference on Pattern Recognition, Vienna, Austria, 3:303-307, Aug. 25-29, 1996.

Willemsen, "Plotting and Piloting—Marine Navigation Courses: Lines of Position, Position Fixes: 4 Plotting and Piloting," http://www.sailingissues.com/navcourse4.html, Oct. 12, 2009, 12 pages.

Wu, "On Optimal Deployment of Probabilistic Detectors in the Plane," System Science Master Project Defense, Louisiana State University, Baton Rouge, Louisiana, Apr. 10, 2002, 1 page. (Abstract only).

Extended European Search Report, dated Oct. 10, 2014, regarding Application No. EP09168308.6, 6 pages.

* cited by examiner

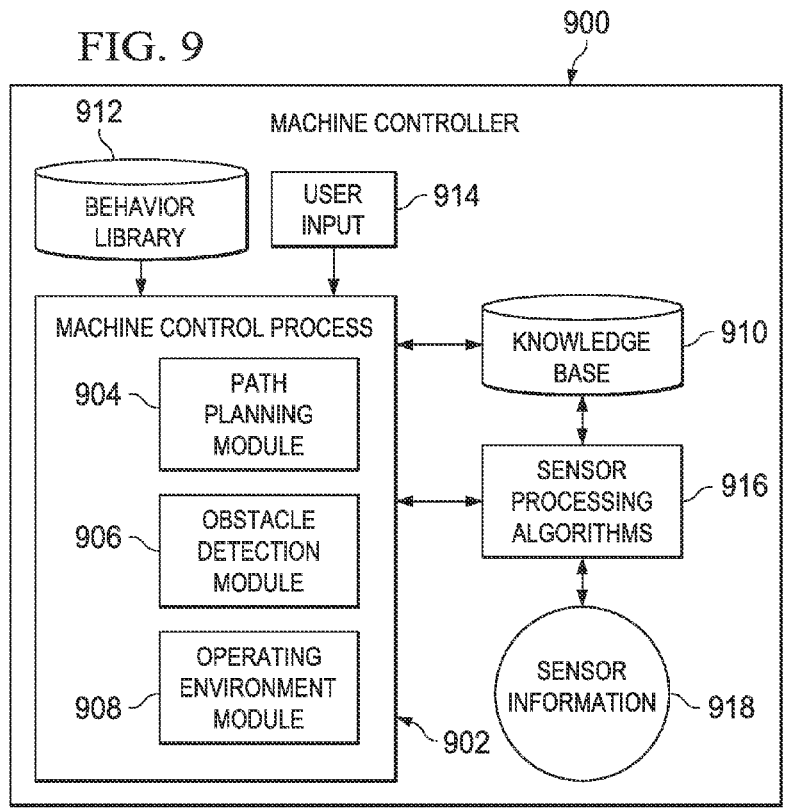
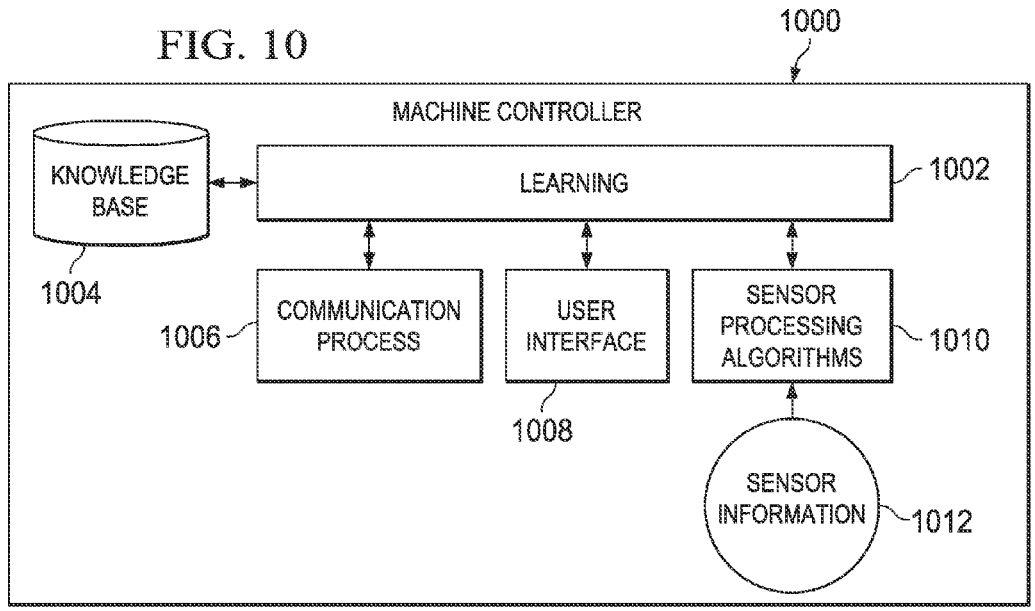

FIG. 11

| | NORMAL OPERATING CONDITIONS 1104 | EARLY FALL 1108 | WINTER 1112 | NOTES |
|---|---|---|---|---|
| GPS 1102 | GOOD TO POOR QUALITY SIGNAL RECEPTION 1106 | GOOD TO POOR QUALITY SIGNAL RECEPTION 1110 | GOOD TO VERY GOOD SIGNAL RECEPTION 1114 | USE AS SEED FOR MAP MATCHING |
| VISIBLE CAMERA IMAGES OF A CURB OR STREET EDGE 1116 | EXCELLENT QUALITY IMAGES 1118 | UNUSABLE QUALITY IMAGES 1120 | UNUSABLE QUALITY IMAGES 1122 | |
| VISIBLE CAMERA IMAGES (8 FT. UP) 1124 | EXCELLENT QUALITY IMAGES 1126 | EXCELLENT QUALITY IMAGES 1128 | GOOD TO EXCELLENT QUALITY IMAGES 1130 | |
| VISIBLE CAMERA IMAGES OF THE STREET CROWN 1132 | GOOD QUALITY IMAGES 1134 | GOOD TO POOR QUALITY IMAGES 1136 | UNUSABLE QUALITY IMAGES 1138 | |
| LIDAR IMAGES OF A CURB 1140 | EXCELLENT 1142 | UNUSABLE 1144 | UNUSABLE 1144 | |
| LIDAR (8 FT. UP) 1146 | EXCELLENT 1148 | EXCELLENT 1148 | EXCELLENT 1148 | |
| LIDAR (SKY) 1150 | UNUSABLE DUE TO CANOPY 1152 | UNUSABLE TO POOR 1154 | EXCELLENT 1156 | |

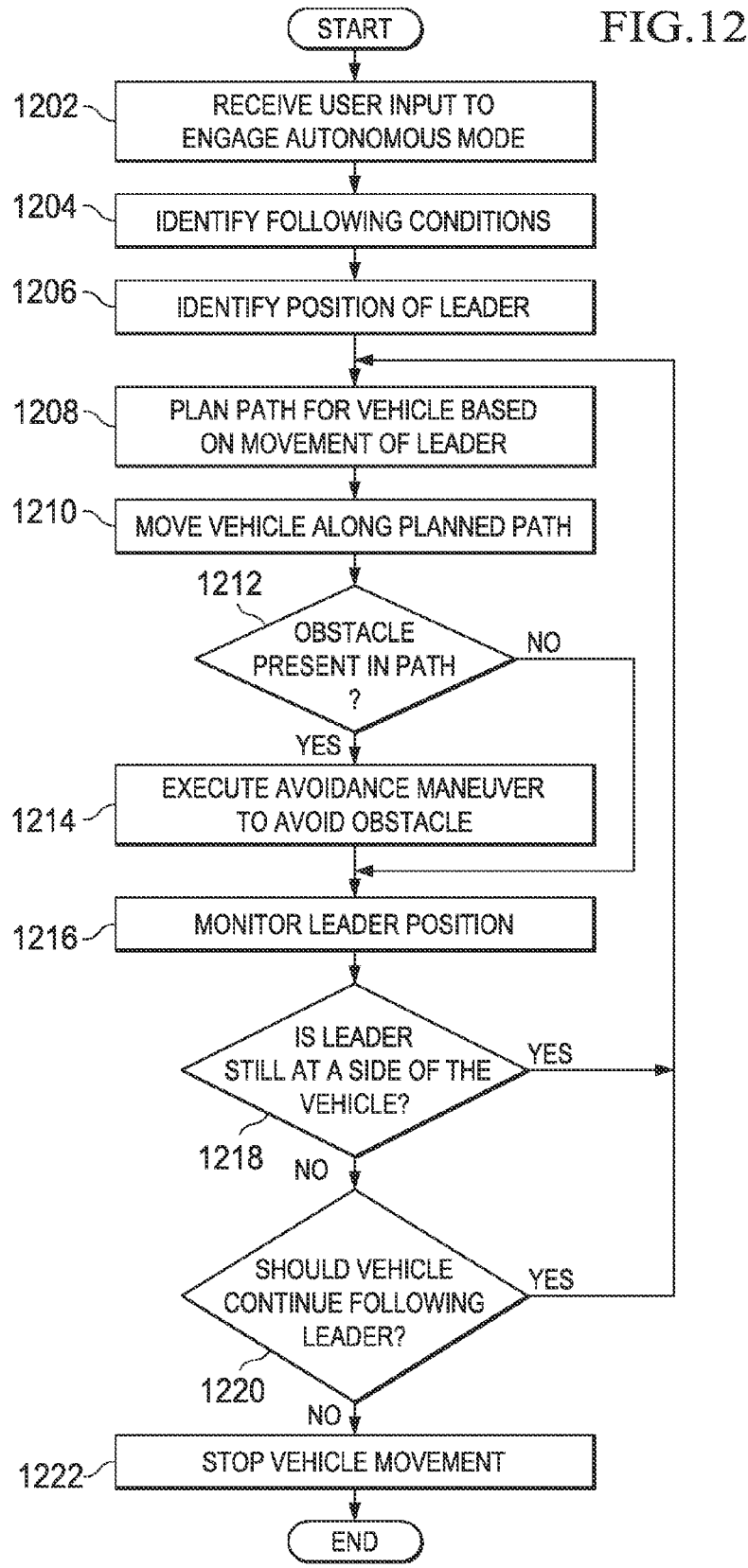

LEADER-FOLLOWER FULLY-AUTONOMOUS VEHICLE WITH OPERATOR ON SIDE

CROSS REFERENCE TO RELATED APPLICATIONS

This application is a continuation-in-part of U.S. patent application Ser. No. 12/329,930, filed on Dec. 8, 2008 and entitled "Garment for Use Near Autonomous Machines" which is a continuation-in-part of the following: U.S. patent application Ser. No. 12/208,752, filed on Sep. 11, 2008 and entitled "Leader-Follower Semi-Autonomous Vehicle with Operator on Side"; U.S. patent application Ser. No. 12/208, 659, filed on Sep. 11, 2008 and entitled "Leader-Follower Fully-Autonomous Vehicle with Operator on Side", now issued as U.S. Pat. No. 8,229,618 on Jul. 24, 2012; U.S. patent application Ser. No. 12/208,691, filed on Sep. 11, 2008 and entitled "High Integrity Perception for Machine Localization and Safeguarding"; U.S. patent application Ser. No. 12/208, 851, filed on Sep. 11, 2008 and entitled "Vehicle With High Integrity Perception System"; U.S. patent application Ser. No. 12/208,885, filed on Sep. 11, 2008 and entitled "Multi-Vehicle High Integrity Perception", now issued as U.S. Pat. No. 8,195,358 on Jun. 5, 2012; and U.S. patent application Ser. No. 12/208,710, filed on Sep. 11, 2008 and entitled "High Integrity Perception Program."

FIELD OF THE INVENTION

The present disclosure relates generally to systems and methods for vehicle operation and more particularly to systems and methods for following an operator of a vehicle. Still more specifically, the present disclosure relates to a method and system utilizing a versatile robotic control module for controlling the autonomous operation of a vehicle.

BACKGROUND OF THE INVENTION

An increasing trend towards developing automated or semi-automated equipment is present in today's work environment. In some situations with the trend, this equipment is completely different from the operator-controlled equipment that is being replaced, and does not allow for any situations in which an operator can be present or take over operation of the vehicle. Such unmanned equipment can be unreliable due to the complexity of systems involved, the current status of computerized control, and uncertainty in various operating environments. As a result, semi-automated equipment is more commonly used. This type of equipment is similar to previous operator-controlled equipment, but incorporates one or more operations that are automated rather than operator-controlled. This semi-automated equipment allows for human supervision and allows the operator to take control when necessary.

SUMMARY

The illustrative embodiments provide a method and apparatus for controlling movement of a vehicle. Movement of an operator located at a side of the vehicle is identified with a plurality of sensors located in the vehicle and the vehicle is moved in a path that maintains the operator at the side of the vehicle while the operator is moving.

The features, functions, and advantages can be achieved independently in various embodiments of the present invention or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and advantages thereof, will best be understood by reference to the following detailed description of an illustrative embodiment of the present invention when read in conjunction with the accompanying drawings, wherein:

FIG. 9 is a block diagram of a vehicle automation system illustrating data flow between components in a machine controller executing a side-following process in accordance with an illustrative embodiment;

FIG. 10 is a block diagram of a learned knowledge base illustrating data flow between components managing a knowledge base in accordance with an illustrative embodiment;

FIG. 11 is a block diagram of a format in a knowledge base used to select sensors for use in planning paths and obstacle avoidance in accordance with an illustrative embodiment;

FIG. 12 is a flowchart illustrating a process for side-following in accordance with an illustrative embodiment;

DESCRIPTION OF THE PREFERRED EMBODIMENT

Figure 1:
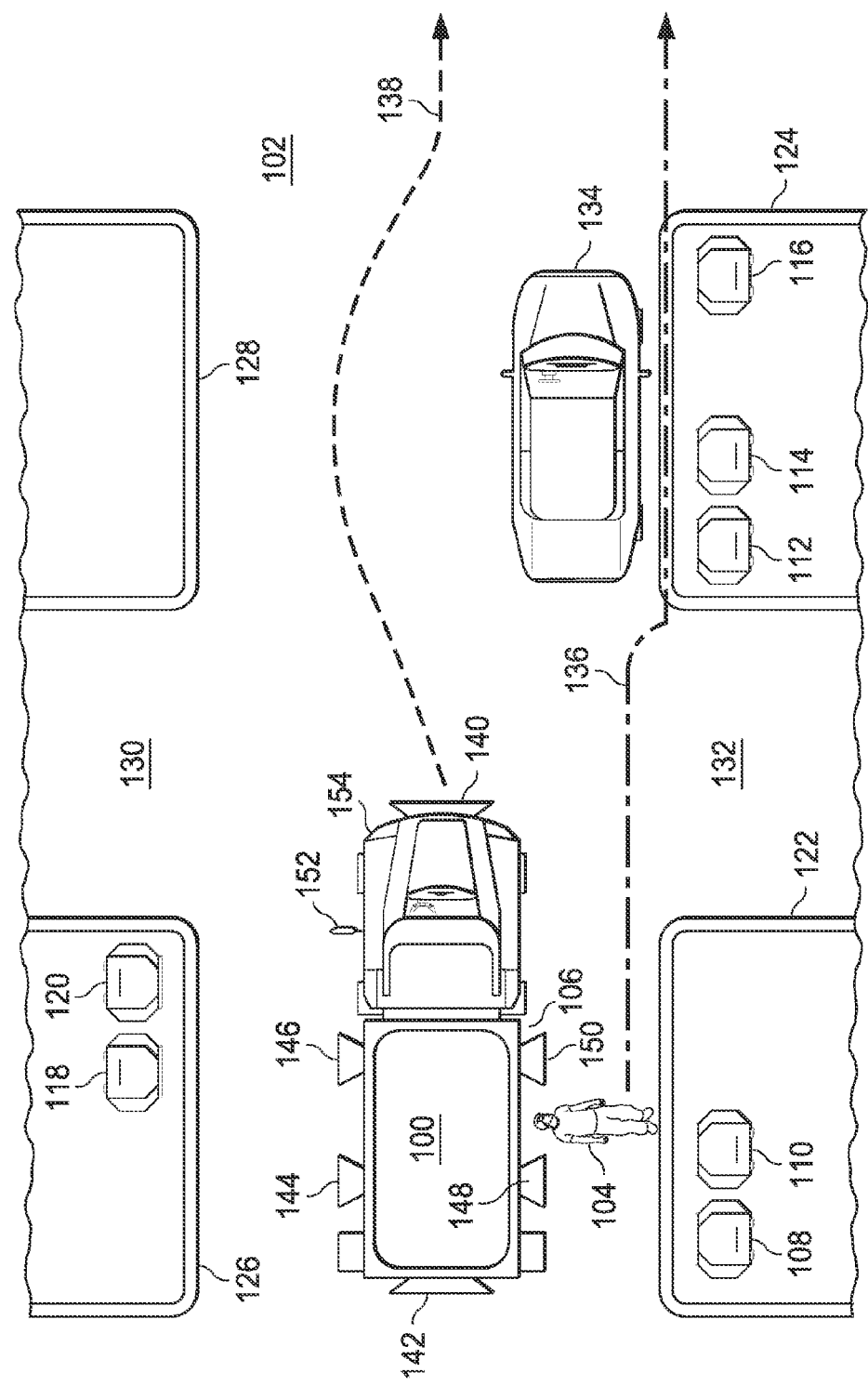
FIG. 1 is a block diagram of a vehicle operating a leader/follower mode with an operator located to the side of the vehicle in accordance with an illustrative embodiment.

Embodiments of this invention provide systems and methods for vehicle operation and more particularly systems and methods for following an operator of a vehicle. Still more specifically, embodiments of this invention provide a method and system utilizing a versatile robotic control module for controlling the autonomous operation of a vehicle.

Robotic or autonomous vehicles, sometimes referred to as mobile robotic platforms, generally have a robotic control system that controls the operational systems of the vehicle. In a vehicle that is limited to a transportation function, the operational systems may include steering, braking, transmission, and throttle systems. Such autonomous vehicles generally have a centralized robotic control system for control of the operational systems of the vehicle. Some military vehicles have been adapted for autonomous operation. In the United States, some tanks, personnel carriers, Stryker vehicles, and other vehicles have been adapted for autonomous capability. Generally, these are to be used in a manned mode as well.

The standard teleoperation system, standard robotics system, and common robotics system by Omnitech Robotics International located in Englewood, Colo. were attempts to provide a kit adaptable to a wide range of vehicles for teleoperation. The standard teleoperation system, standard robotics system, and common robotics system are robust packaging for a wide variety of functional units. For example, each of a vehicle control unit, power system unit, system input/output unit, mobile radio unit, video multiplexer unit, and numerous other system elements is a separately packaged unit that must be connected to the others via controller area network bus or RS-232 serial connections. One element, a 17 kilogram, 8 liter "high integration actuator", includes a linear actuator, or motor, as well as position and feedback sensors; a power amplifier; a digital server processor, and a microcontroller with a controller area network interface. The processor and microcontroller are used to control the motor bound in the package, and are not reconfigurable or available to different or other controls outside motors or sensors. This unit is essentially an integrated motor package, a so-called "smart actuator."

While Omnitech's standard robotics system has been adapted to a wide range of vehicles, including tractors, forklifts, earthmovers, and mine clearing tanks, this system has several shortcomings for autonomous/manual use. This system is slightly more integrated than other systems, but only when using its own actuators. The different illustrative embodiments recognize that this system lacks a number of capabilities. For example, the system lacks any capability for high-bandwidth communications, such as carrying interpretable and interpreted sensor data to supervisory robotics controls, which is necessary for autonomous use. No component, including the vehicle control unit, includes sufficient processing power for autonomous behaviors. Also the different illustrative embodiments recognize that in lacking the capability for autonomous control, the standard robotics system inherently lacks the ability for autonomous safety management, for example, partial teleoperation in which obstacle avoidance behavior can override operator control. The standard robotic system is restricted to its own actuator suite. A separate power supply is part of the system, but this may not be suitable for laser scanners or radios, which, among other components, are sensitive to power quality and to electromagnetic noise.

The different illustrative embodiments recognize that robotic control system sensor inputs may include data associated with the vehicle's destination, preprogrammed path information, and detected obstacle information. Based on such data associated with the information above, the vehicle's movements are controlled. Obstacle detection systems within a vehicle commonly use scanning lasers to scan a beam over a field of view, or cameras to capture images over a field of view. The scanning laser may cycle through an entire range of beam orientations, or provide random access to any particular orientation of the scanning beam. The camera or cameras may capture images over the broad field of view, or of a particular spectrum within the field of view. For obstacle detection applications of a vehicle, the response time for collecting image data should be rapid over a wide field of view to facilitate early recognition and avoidance of obstacles.

Location sensing devices include odometers, global positioning systems, and vision-based triangulation systems. Many location sensing devices are subject to errors in providing an accurate location estimate over time and in different geographic positions. Odometers are subject to material errors due to surface terrain. Satellite-based guidance systems, such as global positioning system-based guidance systems, which are commonly used today as a navigation aid in cars, airplanes, ships, computer-controlled harvesters, mine trucks, and other vehicles, may experience difficulty guiding when heavy foliage or other permanent obstructions, such as mountains, buildings, trees, and terrain, prevent or inhibit global positioning system signals from being accurately received by the system. Vision-based triangulation systems may experience error over certain angular ranges and distance ranges because of the relative position of cameras and landmarks.

The illustrative embodiments also recognize that in order to provide a system and method where an operator may safely and naturally interact with a combination manned/autonomous vehicle, specific mechanical accommodations for intuitive operator use of mode switching systems is required. Therefore, it would be advantageous to have a method and apparatus to provide additional features for autonomous operation of vehicles.

With reference to the figures and in particular with reference to FIG. 1, embodiments of the present invention may be used in a variety of vehicles, such as automobiles, trucks, and utility vehicles.

FIG. 1 depicts a block diagram of a vehicle operating in a leader/follower mode with an operator located to the side of the vehicle in accordance with an illustrative embodiment. FIG. 1 depicts an illustrative environment including an illustrative vehicle 100 in one embodiment of the present invention. In this example, vehicle 100 is a six-wheeled, diesel powered utility vehicle, such as a waste collection vehicle, which may navigate along street 102 in a leader/follower mode with operator 104 located on side 106 of vehicle 100. In this example, vehicle 100 may be used to collect waste from waste containers 108, 110, 112, 114, 116, 118, and 120. As illustrated, waste containers 108 and 110 are located near curb 122, while waste containers 112, 114, and 116 are located near curb 124. Waste containers 118 and 120 are located near curb 126. No waste containers are present near curb 128 in this example. Driveway 130 and driveway 132 leads into street 102 in this illustrative example. In addition, truck 134 is parked by curb 124 in this illustration.

Vehicle 100 may move along street 102 following operator 104 located at side 106 using a number of different modes of operation to aid operator 104 in collecting waste from waste containers 108, 110, 112, 114, 116, 118, and 120. The modes include, for example, a side following mode, a teach and playback mode, a teleoperation mode, a path mapping mode, a straight mode, and other suitable modes of operation. An operator may be a person being followed as the leader when the vehicle is operating in a side-following mode, a person driving the vehicle, or a person controlling the vehicle movements in teleoperation mode.

In the side following mode, operator 104 is the leader and vehicle 100 is the follower. Operator 104, however, does not need to be located on front 154 of vehicle 100 for vehicle 100 to follow operator 104. In one illustrative embodiment, for example in a garbage collection implementation, the vehicle will follow the operator forward, but not sideways or backwards when the operator collects each of several waste containers at a curbside and empties the contents of each container into the back of the vehicle. In this example, the vehicle moves forward to align the back of the vehicle with the waste containers and/or the operator and then stops. The operator can empty the waste containers at that location. Then, by user input or by the operator moving forward past a defined location on the vehicle, the operator signals the vehicle to resume its forward progress.

Operator 104 may leave vehicle 100 and place waste material in waste containers 108 and 110 into vehicle 100. Operator 104 may then walk along path 136 to collect and place waste materials from waste containers 112, 114, and 116 into vehicle 100. As operator 104 walks along path 136, vehicle 100 may follow along path 136, maintaining operator 104 at side 106 of vehicle 100. In these examples, vehicle 100 may maintain a substantially parallel path to operator 104 with deviations for obstacles. Vehicle 100, in this example, may include the capability of maneuvering around obstacles, such as, for example, truck 134. As can be seen in this example, path 138 shows vehicle 100 avoiding truck 134 while following operator 104.

Vehicle 100 may locate operator 104 and various obstacles using a sensor system. In these examples, the sensor system includes forward sensor 140, rear sensor 142, side sensor 144, side sensor 146, side sensor 148, side sensor 150, and rear looking side sensor 152. The depicted sensors may be used to detect the environment around vehicle 100. This environment includes various objects, such as, for example, operator 104, waste containers 108 and 110, curb 122, waste containers 118 and 120, curb 126, driveway 132, driveway 130, truck 134, and other suitable objects. Other objects that may be detected include, for example, trees, light poles, intersections, and other suitable features that may be in the environment around vehicle 100.

The depicted sensors are only examples of some sensors that may be used to detect the location of operator 104 and any potential obstacles. Sensors 148 and 150 on side 106 may be used to track operator 104. With an ability to track the location of operation 104, vehicle 100 may follow operator 104 as operator 104 moves along path 136. In these different illustrative examples, vehicle 100 identifies the path 136 of operator 104 and generates path 138 to follow or move in a manner parallel to path 136 of operator 104. With this type of operation, operator 104 may collect waste without having to stop, enter vehicle 100, drive vehicle 100 to the next collection point, and exit vehicle 100. Also, the need for another operator to drive vehicle 100 is unnecessary in the depicted examples.

The side following mode may include preprogrammed maneuvers in which operator 104 may change the movement of vehicle 100 from an otherwise straight travel path for vehicle 100. For example, with truck 134 parked on street 102, operator 104 may initiate a go around car maneuver that causes vehicle 100 to steer out and around truck 134 in a preset path as shown in path 138. With this mode, automatic obstacle identification and avoidance features may still be used.

Another manner in which vehicle 100 may avoid an object, such as truck 134 is to have operator 104 walk a path around the vehicle and then ask the truck to repeat that path. This type of feature may require knowing the position of the operator and recording the path followed by the operator.

With the teach and play back mode, operator 104 may drive vehicle 100 along path 138 on street 102 without stops. Operator 104 may enter way points to indicate where waste containers are located along street 102. These way points may provide points at which vehicle 100 stops to wait for operator 104 to load waste from the waste containers into vehicle 100.

After driving path 138, operator 104 may move vehicle 100 back to the beginning of path 138. In the second pass on street 102, operator 104 may cause vehicle 100 to drive from one way point to another way point. In this manner, vehicle 100 drives from one collection point to another collection point along path 138. Although path 138 may be a set path, vehicle 100 still may include some level of obstacle detection to prevent vehicle 100 from running over or hitting an obstacle, such as truck 134. Additionally, operator 104 may initiate movement from one way point to another way point via a remote control device. Additionally, this remote control device also may allow operator 104 to stop the truck when needed.

In a teleoperation mode, operator 104 may operate or wirelessly drive vehicle 100 down street 102 in a fashion similar to other remote controlled vehicles. This type of mode may be used by operator 104 located at side 106 of vehicle 100. With this type of mode of operation, operator 104 may control vehicle 100 through a wireless controller.

In a path mapping mode, the different paths may be mapped by operator 104 prior to reaching street 102. With the waste collection example, routes may be identical for each trip and operator 104 may rely on the fact that vehicle 100 will move along the same path each time. Intervention or deviation from the mapped path may occur only when an obstacle is present. Again, with the path mapping mode, way points may be set to allow vehicle 100 to stop at waste collection points.

In a straight mode, vehicle 100 may be placed in the middle or offset from some distance from a curb on street 102. Vehicle 100 may move down the street along a straight line allowing one or more operators to walk on either side of vehicle 100 to collect waste. In this type of mode of operation, the path of vehicle 100 is always straight unless an obstacle is encountered. In this type of mode of operation, operator 104 may start and stop vehicle 100 as needed. This type of mode may minimize the intervention needed by a driver.

In different illustrative embodiments, the different types of mode of operation may be used in combination to achieve the desired goals. In these examples, at least one of these modes of operation may be used to minimize driving while maximizing safety and efficiency in a waste collection process. As used herein the phrase "at least one of" when used with a list of items means that different combinations one or more of the items may be used and only one of each item in the list may be needed. For example, "at least one of item A, item B, and item C" may include, for example, without limitation, item A or item A and item B. This example also may include item A, item B, and item C or item B and item C. As another example, at least one of item A, item B, and item C may include item A, two of item B, and 4 of item C.

Further, autonomous routes may include several straight blocks. In other examples, a path may go around blocks in a square or rectangular pattern. Of course, other types of patterns also may be used depending upon the particular implementation. In these examples, operator 104 may drive vehicle 100 onto a block or to a beginning position of a path. Operator 104 also may monitor vehicle 100 for safe operation and ultimately provide overriding control for the behavior of vehicle 100.

In these examples, path 138 may be a preset path, a path that is continuously planned with changes made by vehicle 100 to follow operator 104 in a side following mode, a path that is directed by the operator using remote control in a teleoperation mode, or some other path. Path 138 may be any length depending on the implementation.

Thus, the different illustrative embodiments provide a number of different modes to operate vehicle 100. Although FIG. 1 illustrates a vehicle for waste collection, this illustration is not meant to limit the manner in which different modes may be applied. For example, the different illustrative embodiments may be applied to other types of vehicles and other types of uses. As a specific example, the different illustrative embodiments may be applied to a military vehicle in which a soldier uses a side following mode to provide a shield across a clearing. In other embodiments, vehicle 100 may take the form of an agricultural vehicle. With this type of implementation, the vehicle may have a chemical sprayer mounted and follow an operator as the operator applies chemicals to crops or other foliage. These types of modes also may provide obstacle avoidance and remote control capabilities. As yet another example, the different illustrative embodiments may be applied to delivery vehicles, such as those for the post office or other commercial delivery vehicles.

Figure 2:
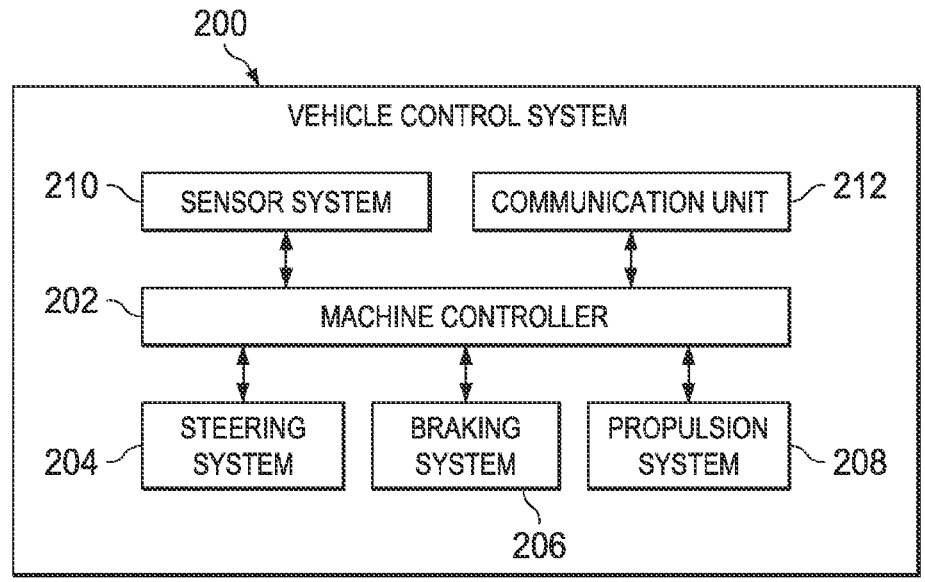
FIG. 2 is a block diagram of components used to control a vehicle in accordance with an illustrative embodiment.

With reference now to FIG. 2, a block diagram of components used to control a vehicle is depicted in accordance with an illustrative embodiment. In this example, vehicle control system 200 is an example of a vehicle control system that may be implemented in a vehicle, such as vehicle 100 in FIG. 1. In this example, vehicle control system 200 includes machine controller 202, steering system 204, braking system 206, propulsion system 208, sensor system 210, and communication unit 212.

Machine controller 202 may be, for example, a data processing system or some other device that may execute processes to control movement of a vehicle. Machine controller 202 may be, for example, a computer, an application integrated specific circuit, or some other suitable device. Machine controller 202 may execute processes to control steering system 204, braking system 206, and propulsion system 208 to control movement of the vehicle. Machine controller 202 may send various commands to these components to operate the vehicle in different modes of operation. These commands may take various forms depending on the implementation. For example, the commands may be analog electrical signals in which a voltage and/or current change is used to control these systems. In other implementations, the commands may take the form of data sent to the systems to initiate the desired actions.

Steering system 204 may control the direction or steering of the vehicle in response to commands received from machine controller 202. Steering system 204 may be, for example, an electrically controlled hydraulic steering system, an electrically driven rack and pinion steering system, an Ackerman steering system, or some other suitable steering system.

Braking system 206 may slow down and/or stop the vehicle in response to commands from machine controller 202. Braking system 206 may be an electrically controlled braking system. This braking system may be, for example, a hydraulic braking system, a friction braking system, or some other suitable braking system that may be electrically controlled.

In these examples, propulsion system 208 may propel or move the vehicle in response to commands from machine controller 202. Propulsion system 208 may maintain or increase the speed at which a vehicle moves in response to instructions received from machine controller 202. Propulsion system 208 may be an electrically controlled propulsion system. Propulsion system 208 may be, for example, an internal combustion engine, an internal combustion engine/electric hybrid system, an electric engine, or some other suitable propulsion system.

Sensor system 210 may be a set of sensors used to collect information about the environment around a vehicle. In these examples, the information is sent to machine controller 202 to provide data in identifying how the vehicle should move in different modes of operation. In these examples, a set refers to one or more items. A set of sensors is one or more sensors in these examples.

Communication unit 212 may provide communications links to machine controller 202 to receive information. This information includes, for example, data, commands, and/or instructions. Communication unit 212 may take various forms. For example, communication unit 212 may include a wireless communications system, such as a cellular phone system, a Wi-Fi wireless system, a Bluetooth wireless system, or some other suitable wireless communications system. Further, communication unit 212 also may include a communications port, such as, for example, a universal serial bus port, a serial interface, a parallel port interface, a network interface, or some other suitable port to provide a physical communications link. Communication unit 212 may be used to communicate with a remote location or an operator.

Figure 3:
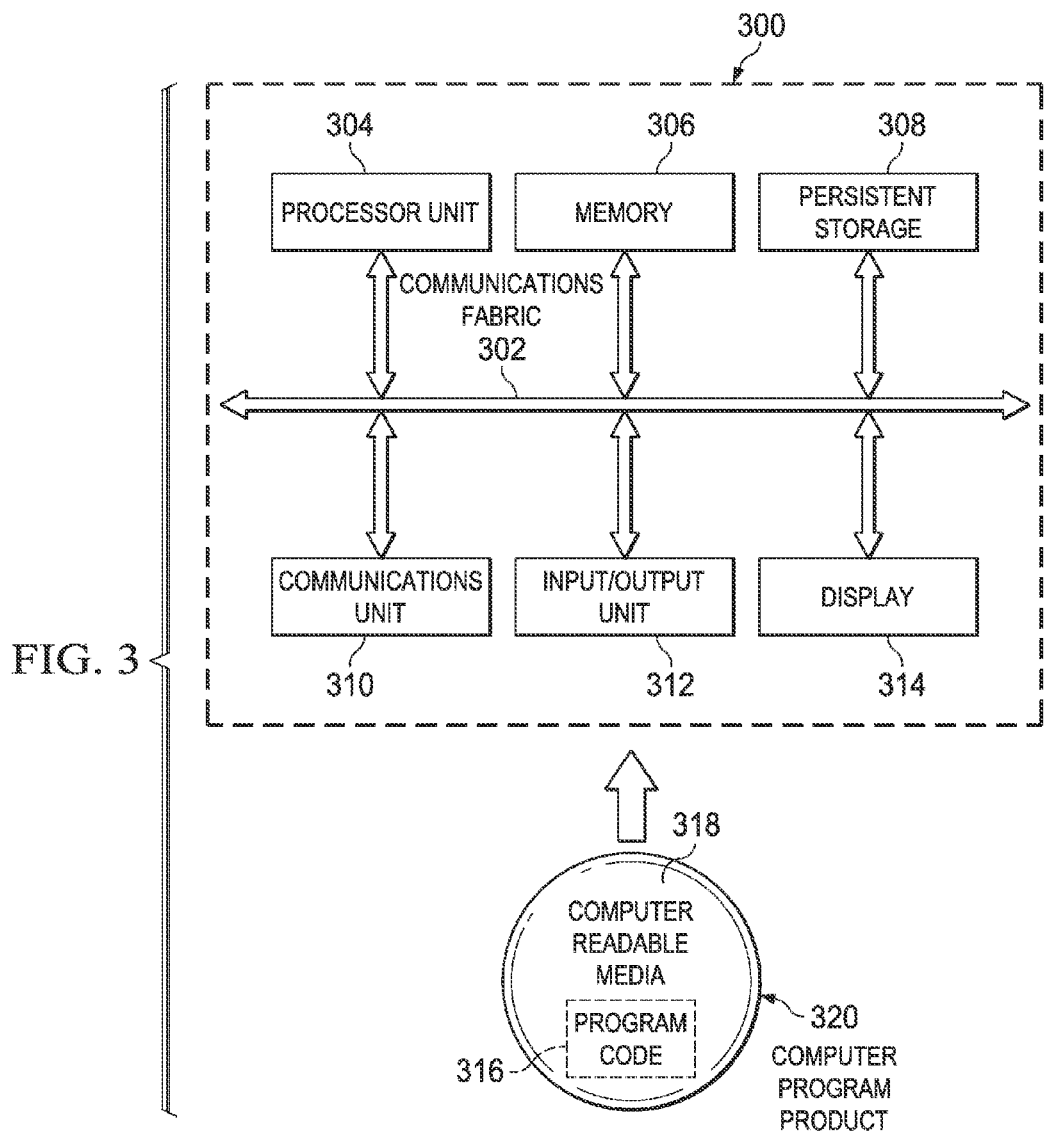
FIG. 3 is a block diagram of a data processing system in accordance with an illustrative embodiment.

With reference now to FIG. 3, a block diagram of a data processing system is depicted in accordance with an illustrative embodiment. Data processing system 300 is an example of one manner in which machine controller 202 in FIG. 2 may be implemented. In this illustrative example, data processing system 300 includes communications fabric 302, which provides communications between processor unit 304, memory 306, persistent storage 308, communications unit 310, input/output (I/O) unit 312, and display 314.

Processor unit 304 serves to execute instructions for software that may be loaded into memory 306. Processor unit 304 may be a set of one or more processors or may be a multi-processor core, depending on the particular implementation. Further, processor unit 304 may be implemented using one or more heterogeneous processor systems in which a main processor is present with secondary processors on a single chip. As another illustrative example, processor unit 304 may be a symmetric multi-processor system containing multiple processors of the same type.

Memory 306 and persistent storage 308 are examples of storage devices. A storage device is any piece of hardware that is capable of storing information either on a temporary basis and/or a permanent basis. Memory 306, in these examples, may be, for example, a random access memory or any other suitable volatile or non-volatile storage device. Persistent storage 308 may take various forms depending on the particular implementation. For example, persistent storage 308 may contain one or more components or devices. For example, persistent storage 308 may be a hard drive, a flash memory, a rewritable optical disk, a rewritable magnetic tape, or some combination of the above. The media used by persistent storage 308 also may be removable. For example, a removable hard drive may be used for persistent storage 308.

Communications unit 310, in these examples, provides for communications with other data processing systems or devices. In these examples, communications unit 310 is a network interface card. Communications unit 310 may provide communications through the use of either or both physical and wireless communications links.

Input/output unit 312 allows for input and output of data with other devices that may be connected to data processing system 300. For example, input/output unit 312 may provide a connection for user input through a keyboard and mouse. Further, input/output unit 312 may send output to a printer. Display 314 provides a mechanism to display information to a user.

Instructions for the operating system and applications or programs are located on persistent storage 308. These instructions may be loaded into memory 306 for execution by processor unit 304. The processes of the different embodiments may be performed by processor unit 304 using computer implemented instructions, which may be located in a memory, such as memory 306. These instructions are referred to as program code, computer usable program code, or computer readable program code that may be read and executed by a processor in processor unit 304. The program code in the different embodiments may be embodied on different physical or tangible computer readable media, such as memory 306 or persistent storage 308.

Program code 316 is located in a functional form on computer readable media 318 that is selectively removable and may be loaded onto or transferred to data processing system 300 for execution by processor unit 304. Program code 316 and computer readable media 318 form computer program product 320 in these examples. In one example, computer readable media 318 may be in a tangible form, such as, for example, an optical or magnetic disc that is inserted or placed into a drive or other device that is part of persistent storage 308 for transfer onto a storage device, such as a hard drive that is part of persistent storage 308. In a tangible form, computer readable media 318 also may take the form of a persistent storage, such as a hard drive, a thumb drive, or a flash memory that is connected to data processing system 300. The tangible form of computer readable media 318 is also referred to as computer recordable storage media. In some instances, computer readable media 318 may not be removable.

Alternatively, program code 316 may be transferred to data processing system 300 from computer readable media 318 through a communications link to communications unit 310 and/or through a connection to input/output unit 312. The communications link and/or the connection may be physical or wireless in the illustrative examples. The computer readable media also may take the form of non-tangible media, such as communications links or wireless transmissions containing the program code.

The different components illustrated for data processing system 300 are not meant to provide architectural limitations to the manner in which different embodiments may be implemented. The different illustrative embodiments may be implemented in a data processing system including components in addition to or in place of those illustrated for data processing system 300. Other components shown in FIG. 3 can be varied from the illustrative examples shown. As one example, a storage device in data processing system 300 is any hardware apparatus that may store data. Memory 306, persistent storage 308, and computer readable media 318 are examples of storage devices in a tangible form.

In another example, a bus system may be used to implement communications fabric 302 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 306 or a cache, such as found in an interface and memory controller hub that may be present in communications fabric 302.

Figure 4:
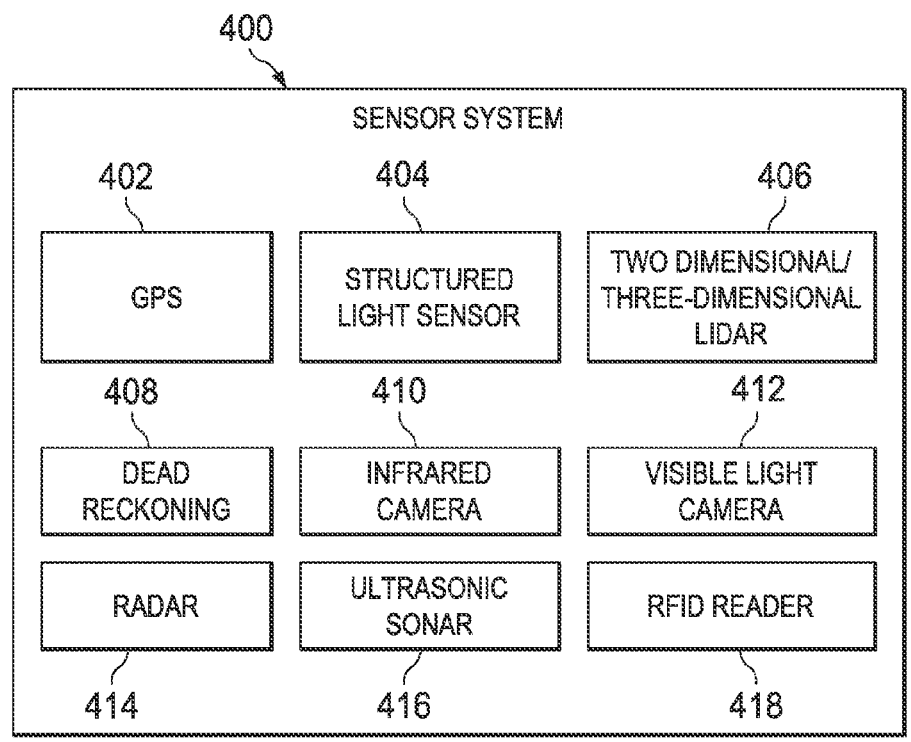
FIG. 4 is a block diagram of a sensor system in accordance with an illustrative embodiment.

With reference now to FIG. 4, a block diagram of a sensor system is depicted in accordance with an illustrative embodiment. Sensor system 400 is an example of one implementation of sensor system 210 in FIG. 2. As illustrated, sensor system 400 includes, for example, global positioning system 402, structured light sensor 404, two dimensional/three dimensional lidar 406, dead reckoning 408, infrared camera 410, visible light camera 412, radar 414, ultrasonic sonar 416, and radio frequency identification reader 418. These different sensors may be used to identify the environment around a vehicle. The sensors in sensor system 400 may be selected such that one of the sensors is always capable of sensing information needed to operate the vehicle in different operating environments.

Global positioning system 402 may identify the location of the vehicle with respect to other objects in the environment. Global positioning system 402 may be any type of radio frequency triangulation scheme based on signal strength and/or time of flight. Examples include, without limitation, the Global Positioning System, Glonass, Galileo, and cell phone tower relative signal strength. Position is typically reported as latitude and longitude with an error that depends on factors, such as ionispheric conditions, satellite constellation, and signal attenuation from vegetation.

Structured light sensor 404 emits light in a pattern, such as one or more lines, reads back the reflections of light through a camera, and interprets the reflections to detect and measure objects in the environment. Two dimensional/three dimensional lidar 406 is an optical remote sensing technology that measures properties of scattered light to find range and/or other information of a distant target. Two dimensional/three dimensional lidar 406 emits laser pulses as a beam, and then scans the beam to generate two dimensional or three dimensional range matrices. The range matrices are used to determine distance to an object or surface by measuring the time delay between transmission of a pulse and detection of the reflected signal.

Dead reckoning 408 begins with a known position, which is then advanced, mathematically or directly, based upon known speed, elapsed time, and course. The advancement based upon speed may use the vehicle odometer, or ground speed radar, to determine distance traveled from the known position. Infrared camera 410 detects heat indicative of a living thing versus an inanimate object. An infrared camera may also form an image using infrared radiation. Visible light camera 412 may be a standard still-image camera, which may be used alone for color information or with a second camera to generate stereoscopic, or three-dimensional images. When visible light camera 412 is used along with a second camera to generate stereoscopic images, the two or more cameras may be set with different exposure settings to provide improved performance over a range of lighting conditions. Visible light camera 412 may also be a video camera that captures and records moving images.

Radar 414 uses electromagnetic waves to identify the range, altitude, direction, or speed of both moving and fixed objects. Radar 414 is well known in the art, and may be used in a time of flight mode to calculate distance to an object, as well as Doppler mode to calculate the speed of an object. Ultrasonic sonar 416 uses sound propagation on an ultrasonic frequency to measure the distance to an object by measuring the time from transmission of a pulse to reception and converting the measurement into a range using the known speed of sound. Ultrasonic sonar 416 is well known in the art and can also be used in a time of flight mode or Doppler mode, similar to radar 414. Radio frequency identification reader 418 relies on stored data and remotely retrieves the data using devices called radio frequency identification (RFID) tags or transponders.

Sensor system 400 may retrieve environmental data from one or more of the sensors to obtain different perspectives of the environment. For example, sensor system 400 may obtain visual data from visible light camera 412, data about the distance of the vehicle in relation to objects in the environment from two dimensional/three dimensional model lidar 406, and location data of the vehicle in relation to a map from global positioning system 402.

Sensor system 400 is capable of detecting objects even in different operating environments. For example, global positioning system 402 may be used to identify a position of the vehicle. If the street has trees with thick canopies during the spring, global positioning system 402 may be unable to provide location information. In this situation, visible light camera 412 and/or two dimensional/three dimensional lidar 406 may be used to identify a location of the vehicle relative to non-mobile objects, such as curbs, light poles, trees, and other suitable landmarks.

In addition to receiving different perspectives of the environment, sensor system 400 provides redundancy in the event of a sensor failure, which facilitates high-integrity operation of the vehicle. For example, in an illustrative embodiment, if visible light camera 412 is the primary sensor used to identify the location of the operator in side-following mode, and visible light camera 412 fails, radio frequency identification reader 418 will still detect the location of the operator through a radio frequency identification tag worn by the operator, thereby providing redundancy for safe operation of the vehicle.

Figure 5:
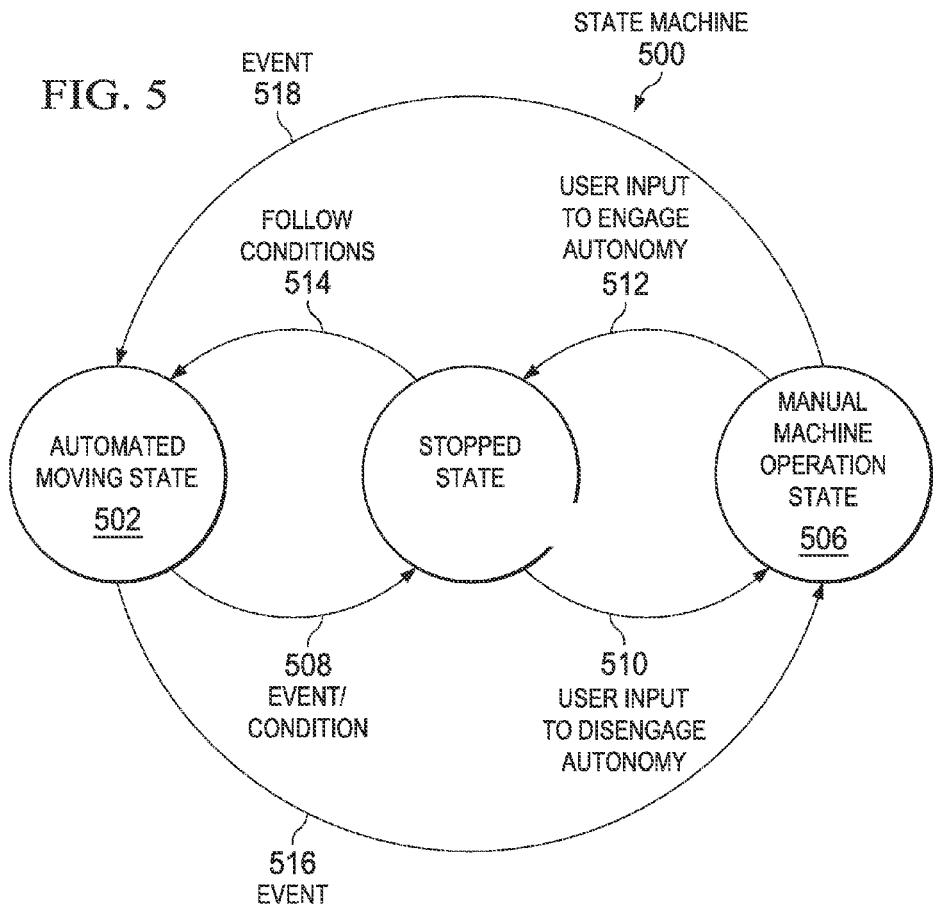
FIG. 5 is a block diagram of a state machine illustrating different modes of operation for a vehicle in accordance with an illustrative embodiment.

With reference now to FIG. 5, a block diagram of a state machine illustrating different modes of operation for a vehicle is depicted in accordance with an illustrative embodiment. In this example, state machine 500 illustrates different states that a vehicle, such as vehicle 100 in FIG. 1, may enter when operating in different modes of operation. State machine 500 may be implemented in a vehicle control system, such as vehicle control system 200 in FIG. 2. In particular, the state machine may be implemented as a set of processes in machine controller 202 in FIG. 2. In this example, state machine 500 includes automated moving state 502, stopped state 504, and manual machine operation state 506.

Automated moving state 502 is a state in which the vehicle may move without user input. For example, the vehicle may move along a preset path or use a side following mode. Stopped state 504 is a state in which the vehicle is stopped. State machine 500 may enter this state if certain conditions are encountered. For example, without limitation, encountering an obstacle or an operator input may cause state machine 500 to enter stopped state 504. An obstacle may be any object that may cause the vehicle to touch, hit, or otherwise encounter the object if the vehicle continues to move its current or planned path. An obstacle may be, for example, a person, a dog, a car, a tree, debris, or other suitable objects. Manual machine operation state 506 is a state in which the vehicle may be operated in response to user input. This user input may be, for example, the operator controlling the vehicle from inside the vehicle in the driver's seat. In other illustrative embodiments, manual machine operation state 506 may involve user input from an operator located outside of the vehicle. The illustration of state machine 500 is not meant to limit the manner in which a state machine may be implemented to control movement of a vehicle. In other illustrative examples, other states may be used in addition to or in place of states illustrated in state machine 500. For example, state machine 500 also may include a remote control state in which operation of the vehicle may be controlled from a remote location, such as, for example, a home office, or a station.

In an illustrative example, a vehicle may be operating in automated moving state 502 when event/condition 508 occurs, automatically transitioning the vehicle mode to stopped state 504. Event/condition 508 may be an event or condition, such as, for example, without limitation, detecting a moving object in the safety zone around the vehicle, detecting an unauthenticated person in the safety zone around the vehicle, detecting a large object or obstacle in the path of the vehicle, detecting a large object moving/approaching the intended area of movement for the vehicle, detecting the authenticated worker near the rear of the vehicle, and the like. In another illustrative example, event/condition 508 may be an emergency stop condition, which would transition the vehicle from automated moving state 502 to stopped state 504 with a hard application of brakes rather than one with fuel economy, labor efficiency, and aesthetic deceleration. The trigger for an emergency stop condition may be inputs, such as, without limitation, an emergency stop button located on the outside of a vehicle being asserted, a safeguarding sensor fault, an unauthenticated person entering the human safety zone around the vehicle, an unauthorized object entering the property safety zone around the vehicle, an object detected as being on trajectory for impact with the vehicle, and the like. User input to disengage autonomy 510 may be received from an operator, which automatically transitions the vehicle mode to manual machine operation state 506. In one illustrative embodiment, event/condition 508 and user input to disengage autonomy 510 are useful for allowing the operator to move from the rear of the vehicle to the driver station.

In another illustrative example, the vehicle may be operating in manual machine operation state 506 when user input to engage autonomy 512 is received. In one illustrative embodiment, the vehicle transitions to stopped state 504 upon receiving user input to engage autonomy 512. The vehicle then identifies follow conditions 514 in order to transition to automated moving state 502. Follow conditions 514 may be conditions, such as, without limitation, identifying an authenticated worker in the safe zone around the vehicle, identifying no unauthenticated person in the safe zone around the vehicle, detecting the authenticated worker towards the front of the vehicle, detecting the authenticated worker at a side of the vehicle, detecting that the position of the authenticated worker is changing towards the next location in a planned path, and the like.

In another illustrative embodiment, a vehicle operating in automated moving state 502 detects event 516 and automatically transitions to manual machine operation state 506 without entering stopped state 504. In another illustrative embodiment, a vehicle operating in manual machine operation state 506 detects event 518 and automatically transitions to automated moving state 502 without entering stopped state 504.

Event 516 may be, for example, an operator manually taking over control of the steering wheel in the vehicle and overriding the automatic steering. In another example, event 516 may be the operator using a user interface to indicate that the vehicle should be in a slightly different relative position as it follows, for example, adjusting the relative position forward, backwards, or to a side. In one example, event 518 may have no user input that is received for a set time period, triggering the vehicle to switch back to automated moving state 502. In another illustrative example, event 516 may be an operator taking manual control of the steering wheel of the vehicle to cross a busy street, and event 518 may be the operator releasing control of the steering wheel once the street is crossed.

Figure 6:
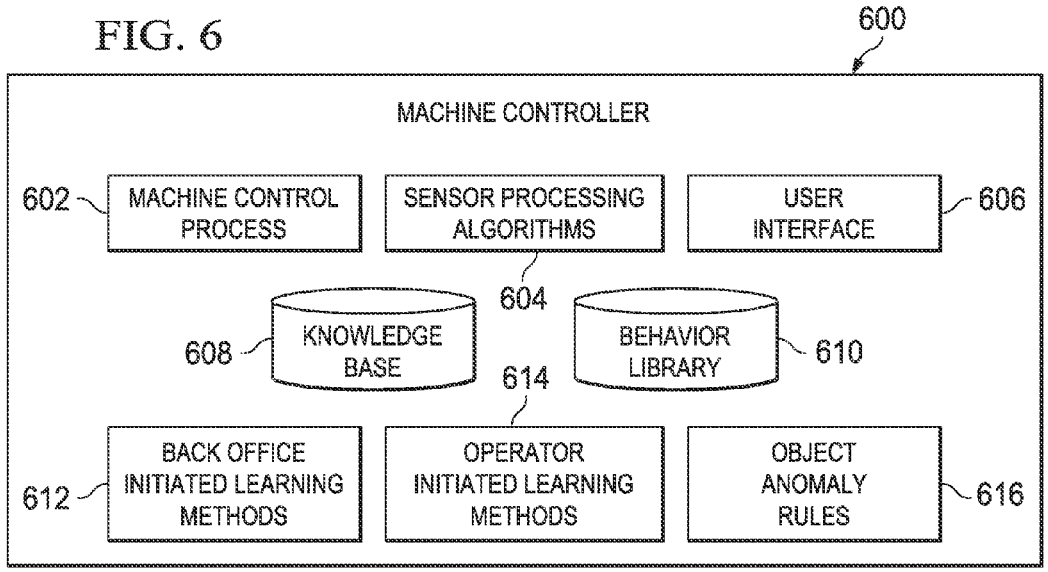
FIG. 6 is a block diagram of functional software components that may be implemented in a machine controller in accordance with an illustrative embodiment.

With reference now to FIG. 6, a block diagram of functional software components that may be implemented in a machine controller is depicted in accordance with an illustrative embodiment. In this example, different functional software components that may be used to control a vehicle are illustrated. The vehicle may be a vehicle, such as vehicle 100 in FIG. 1. Machine controller 600 may be implemented in a vehicle control system, such as vehicle control system 200 in FIG. 2 using a data processing system, such as data processing system 300 in FIG. 3. In this example machine control process 602, sensor processing algorithms 604, user interface 606, knowledge base 608, behavior library 610, back office initiated learning methods 612, operator initiated learning methods 614, and object anomaly rules 616 are present in machine controller 600.

Machine control process 602 transmits signals to steering, braking, and propulsion systems, such as steering system 204, braking system 206, and propulsion system 208 in FIG. 2. Machine control process 602 may also transmit signals to components of a sensor system, such as sensor system 400 in FIG. 4. For example, in an illustrative embodiment, machine control process 602 transmits a signal to a camera component of sensor system 400 in order to pan, tilt, or zoom the camera to acquire different images and perspectives of an environment around the vehicle. Machine control process 602 may also transmit signals to sensors within sensor system 400 in order to activate, deactivate, or manipulate the sensor itself.

Sensor processing algorithms 604 receives sensor data from sensor system 400 and classifies the sensor data into thematic features. This classification may include identifying objects that have been detected in the environment. For example, sensor processing algorithms 604 may classify an object as a person, curb, tree, waste container, light pole, driveway, or some other type of object. The classification may be performed to provide information about objects in the environment. This information may be used to generate a thematic map, which may contain a spatial pattern of attributes. The attributes may include classified objects. The classified objects may include dimensional information, such as, for example, location, height, width, color, and other suitable information. This map may be used to plan actions for the vehicle. The action may be, for example, planning paths to follow an operator in a side following mode or performing object avoidance.

The classification may be done autonomously or with the aid of user input through user interface 606. User interface 606 may be, in one illustrative embodiment, presented on a display monitor mounted on a side of a vehicle and viewable by an operator. User interface 606 may display sensor data from the environment surrounding the vehicle, as well as messages, alerts, and queries for the operator. In other illustrative embodiments, user interface 606 may be presented on a remote display held by the operator. For example, in an illustrative embodiment, sensor processing algorithms 604 receives data from a laser range finder, such as two dimensional/three dimensional lidar 406 in FIG. 4, identifying points in the environment. The information processed by sensor processing algorithms 604 is displayed to an operator through user interface 606. User input may be received to associate a data classifier with the points in the environment, such as, for example, a data classifier of "curb" associated with one point, and "street" with another point. Curb and street are examples of thematic features in an environment. Sensor processing algorithms 604 then interacts with knowledge base 608 to locate the classified thematic features on a thematic map stored in knowledge base 608, and calculates the vehicle position based on the sensor data in conjunction with the landmark localization. Machine control process 602 receives the environmental data from sensor processing algorithms 604, and interacts with knowledge base 608 and behavior library 610 in order to determine which commands to send to the vehicle's steering, braking, and propulsion components.

Knowledge base 608 contains information about the operating environment, such as, for example, a fixed map showing streets, structures, tree locations, and other static object locations. Knowledge base 608 may also contain information, such as, without limitation, local flora and fauna of the operating environment, current weather for the operating environment, weather history for the operating environment, specific environmental features of the work area that affect the vehicle, and the like. The information in knowledge base 608 may be used to perform classification and plan actions.

Behavior library 610 contains various behavioral processes specific to machine coordination that can be called and executed by machine control process 602. In one illustrative embodiment, there may be multiple copies of behavior library 610 on machine controller 600 in order to provide redundancy. The library is accessed by machine control process 602. Back office initiated learning methods 612 interacts with knowledge base 608 and machine control process 602 to maintain the integrity of the environmental and work area data stored in knowledge base 608.

For example, in an illustrative embodiment, if knowledge base 608 has been updated with information indicating a tree on a street is to be cut down, back office initiated learning methods 612 may prompt machine control process 602 to send a signal to sensor system 400 instructing a visible light camera to capture an image of the work area where the tree should be located, according to the thematic map stored in knowledge base 608. Sensor processing algorithms 604 then receives the image and processes the sensor data to determine if the tree still exists or has been removed.

Operator initiated learning methods 614 receives input from an operator via user interface 606 about the current environment and work area encountered by the vehicle. These methods may be used in different modes, such as for example, a teach and playback mode. With this mode, operator initiated learning methods 614 may learn and store a path driven by an operator.

Object anomaly rules 616 provide machine control process 602 instructions on how to operate the vehicle when an anomaly occurs, such as sensor data received by sensor processing algorithms 604 being incongruous with environmental data stored in knowledge base 608. For example, object anomaly rules 616 may include, without limitation, instructions to alert the operator via user interface 606 or instructions to activate a different sensor in sensor system 400 in order to obtain a different perspective of the environment.

Figure 7:
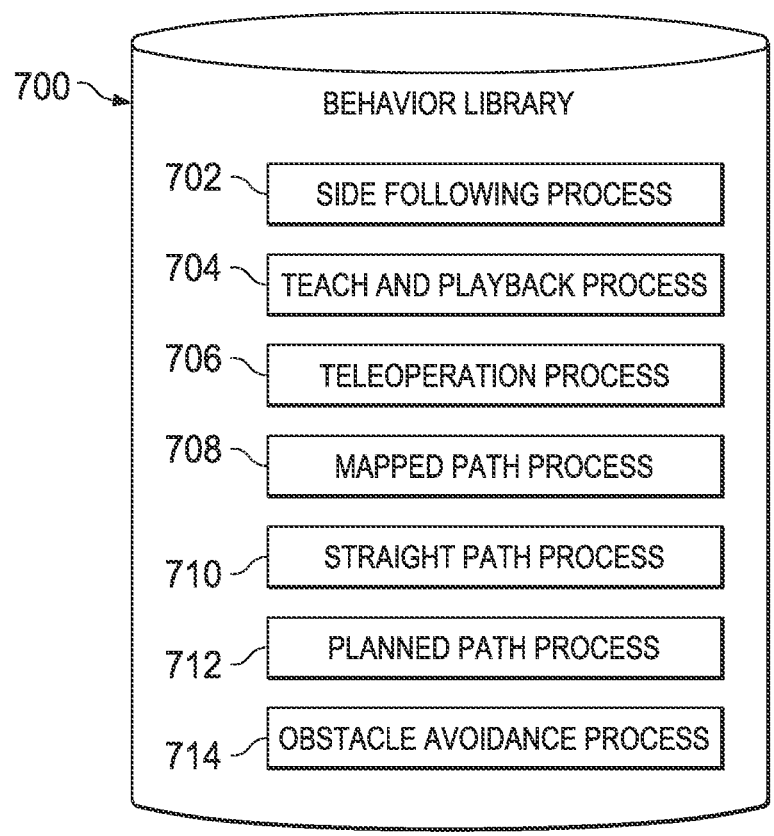
FIG. 7 is a block diagram of components in a behavioral library for controlling a side-following vehicle in accordance with an illustrative embodiment.

With reference now to FIG. 7, a block diagram of components in a behavioral library for controlling a side-following vehicle is depicted in accordance with an illustrative embodiment. Behavior library 700 is an example of a behavior library component of a machine controller, such as behavior library 610 of machine controller 600 in FIG. 6. Behavior library 700 includes various behavioral processes for the vehicle that can be called and executed by a machine control process, such as machine control process 602 in FIG. 6. The behavioral processes depicted in FIG. 7 are only examples of some possible processes and are not meant to limit the invention in any way.

Behavior library 700 includes side following process 702, teach and playback process 704, teleoperation process 706, mapped path process 708, straight path process 710, planned path process 712, and obstacle avoidance process 714.

Side following process 702 is a vehicle behavior in which the vehicle follows an authenticated leader who is walking alongside the vehicle, rather than in front of the vehicle. Teach and playback process 704 is a vehicle behavior in which an operator enters waypoints along a path during a first pass, then allows the vehicle to operate the second pass of the path in an autonomous mode utilizing the waypoints for direction, stopping, and moving the vehicle along the same path. Teleoperation process 706 allows an operator outside the vehicle to operate the vehicle using a wireless radio control. Mapped path process 708 is a behavior that utilizes static route information to direct the vehicle to follow the same path every time. Straight path process 710 is a behavior that directs the vehicle to travel in a straight line from the starting point to the end point, unless an obstacle is encountered. Planned path process 712 utilizes various planned paths stored in knowledge base 608 in FIG. 6 to direct a vehicle down a selected path. Obstacle avoidance process 714 may be used in conjunction with all of the other behavior processes in behavior library 700 to direct the vehicle movement around a detected obstacle.

Figure 8:
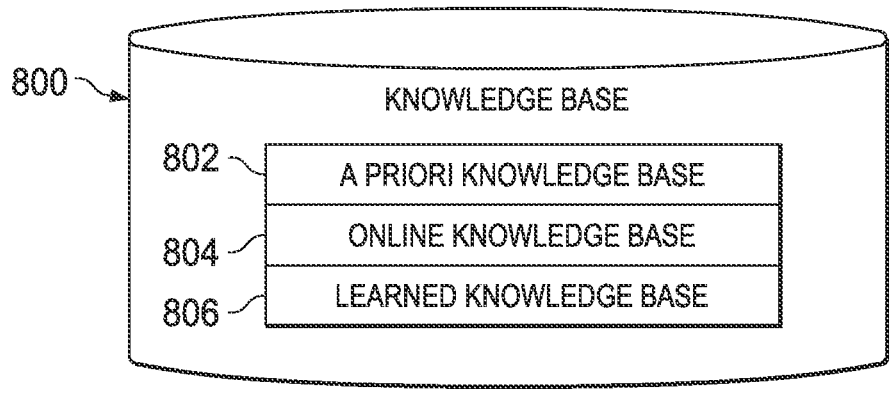
FIG. 8 is a block diagram of a knowledge base in accordance with an illustrative embodiment.

With reference now to FIG. 8, a block diagram of a knowledge base is depicted in accordance with an illustrative embodiment. Knowledge base 800 is an example of a knowledge base component of a machine controller, such as knowledge base 608 of machine controller 600 in FIG. 6. Knowledge base 800 includes a priori knowledge base 802, online knowledge base 804, and learned knowledge base 806.

A priori knowledge base 802 contains static information about the operating environment of a vehicle. Types of information about the operating environment of a vehicle may include, without limitation, a fixed map showing streets, structures, trees, and other static objects in the environment; stored geographic information about the operating environment; and weather patterns for specific times of the year associated with the operating environment. A priori knowledge base 802 may be updated based on information from online knowledge base 804, and learned knowledge base 806.

Online knowledge base 804 interacts with a communications unit, such as communications unit 212 in FIG. 2, to wirelessly access the internet. Online knowledge base 804 automatically provides information to a machine control process which enables adjustment to sensor data processing, site-specific sensor accuracy calculations, and/or exclusion of sensor information. For example, online knowledge base 804 may access the internet to obtain current weather conditions of the operating environment, which may be used by machine control process 602 in FIG. 6 to determine which sensors to activate in order to acquire accurate environmental data for the operating environment. Weather, such as rain, snow, fog, and frost may limit the range of certain sensors, and require an adjustment in attributes of other sensors in order to acquire accurate environmental data from the operating environment.

Other types of information that may be obtained include, without limitation, vegetation information, such as foliage deployment, leaf drop status, lawn moisture stress, and construction activity, which may result in landmarks in certain regions being ignored.

In another illustrative environment, online knowledge base 804 may be used to note when certain activities are in process that affect operation of sensor processing algorithms in machine controller 600. For example, if tree pruning is in progress, a branch matching algorithm should not be used, but a tree trunk matching algorithm may still be used, as long as the trees are not being cut down completely. When the machine controller receives user input signaling that the pruning process is over, the sensor system may collect environmental data to analyze and update a priori knowledge base 802.

Learned knowledge base 806 may be a separate component of knowledge base 800, or alternatively may be integrated with a priori knowledge base 802 in an illustrative embodiment. Learned knowledge base 806 contains knowledge learned as the vehicle spends more time in a specific work area, and may change temporarily or long-term depending upon interactions with online knowledge base 804 and user input. For example, learned knowledge base 806 may detect the absence of a tree that was present the last time it received environmental data from the work area. Learned knowledge base 806 may temporarily change the environmental data associated with the work area to reflect the new absence of a tree, which may later be permanently changed upon user input confirming the tree was in fact cut down. Learned knowledge base 806 may learn through supervised or unsupervised learning.

With reference now to FIG. 9, a block diagram of a vehicle automation system illustrating data flow between components in a machine controller executing a side-following process is depicted in accordance with an illustrative embodiment. Machine controller 900 is an example of machine controller 202 in FIG. 2 and machine controller 600 in FIG. 6. Machine controller 900 includes machine control process 902, path planning module 904, obstacle detection module 906, operating environment module 908, knowledge base 910, behavior library 912, user input 914, sensor processing algorithms 916, and sensor information 918. Machine control process 902 may be operating in autonomous mode or manual machine mode based upon the mode selection of an operator or in response to an event in the environment.

Machine control process 902 transmits signals or commands to steering, braking, and propulsion systems, such as steering system 204, braking system 206, and propulsion system 208 in FIG. 2. Machine control process 902 may also transmit signals or commands to components of a sensor system, such as sensor system 400 in FIG. 4. For example, in an illustrative embodiment, operating in side-following mode, machine control process 902 transmits a signal to a visible light camera component of sensor system 400 in order to adjust the camera settings to acquire an image of the operator. Machine control process 902 may also transmit signals to a radio frequency identification sensor within sensor system 400 in order to activate the sensor to detect a radio frequency identification tag worn by the operator as a failsafe in case the visible light camera fails to acquire an image of the operator. Sensor information 918 may be, in an illustrative example, a camera image of objects in the environment around the vehicle, which is received by sensor processing algorithms 916. Sensor processing algorithms 916 then classifies the objects in the camera image, identifying one object as the operator which the vehicle is to follow in side-following mode. Sensor information 918 may also contain sensor data from the radio frequency identification sensor detecting a radio frequency identification tag on the operator. Machine control process 902 receives the object classification information identifying the operator, as well as the radio frequency identification tag information, and utilizes path planning module 904 to plan a path that follows the movement of the operator. A path may be any length, for example one foot or ten feet, and may change as the operator changes his or her path. Path planning module 904 utilizes information from operating environment 908, sensor processing algorithms 916, knowledge base 910, and behavior library 912 in order to determine what commands machine control process 902 should transmit to steering, braking, and propulsion systems in order to move the vehicle following the movement of the operator.

In an illustrative embodiment, if sensor processing algorithms 916 identifies, through sensor information 918, objects in the environment that are obstacles, machine control process 902 invokes obstacle detection module 906 to temporarily interrupt path planning module 904. Obstacle detection module 906 will override existing commands or signals transmitted to steering, braking, and propulsion systems with obstacle avoidance commands retrieved from behavior library 912.

In another illustrative embodiment, machine control process 902 may operate in a teach and playback mode, receiving user input 914 to invoke a teach and playback process located in behavior library 912. An operator may then drive the vehicle along a path, identifying waypoints through user input 914 at intervals along the path. As each waypoint is received by machine control process 902 through user input 914, machine control process sends a command to a sensor component, such as the global positioning system, to detect the location of the vehicle. Sensor information 918 is received from the global positioning system, and sensor processing algorithms 916 processes the information to identify the location of the vehicle on a map, such as a map of the operating environment stored in knowledge base 910. Path planning module 904 then records the location of the vehicle at each waypoint and the waypoints are associated with the path and stored in knowledge base 910. At a future time, user input 914 may invoke the teach and playback process to autonomously move the vehicle along the path, and then machine control process 902 will retrieve the path and associated waypoints from knowledge base 910 in order to transmit signals or commands to steering, braking, and propulsion systems and move the vehicle along the path. In one illustrative embodiment, machine control process 902 may stop the vehicle at each waypoint and wait for user input 914 to initiate the next action. In another illustrative embodiment, machine control process 902 may pause at each waypoint and wait for detection of forward/movement of the operator along the path before moving to the next waypoint. If sensor processing algorithms 916 identifies an obstacle in the path, obstacle detection module 906 may temporarily interrupt the movement of the vehicle from one waypoint to another waypoint in order to execute obstacle avoidance maneuvers retrieved from behavior library 912.

In another illustrative embodiment, machine control process 902 may operate in a teleoperation mode, receiving user input 914 to invoke a teleoperation process located in behavior library 912. An operator may then drive the vehicle remotely, using, for example, a radio controller to guide the vehicle along a path. Sensor information 918 is received from the sensor system and sensor processing algorithms 916 processes the information to identify any obstacles in the path. In one illustrative embodiment, if sensor processing algorithms 916 identifies an obstacle in the path, obstacle detection module 906 may temporarily interrupt the movement of the vehicle in order to execute obstacle avoidance maneuvers retrieved from behavior library 912. In another illustrative embodiment, if sensor processing algorithms 916 identifies an obstacle in the path, obstacle detection module 906 may alert the operator and wait for user input 914 to execute obstacle avoidance maneuvers.

Operating environment module 908 generates a thematic map of the operating environment around a vehicle. Operating environment module 908 retrieves a static map associated with the operating environment stored in knowledge base 910 and uses the processed information from sensor processing algorithms 916 to identify thematic objects present in the environment and populate the static map to form a thematic map of the operating environment. The thematic map of the operating environment may be used by path planning module 904 for vehicle localization and by obstacle detection module 906 to identify objects in the environment that may be classified as obstacles.

With reference now to FIG. 10, a block diagram of a learned knowledge base illustrating data flow between components managing a knowledge base is depicted in accordance with an illustrative embodiment. Machine controller 1000 is an example of machine controller 202 in FIG. 2. Machine controller 1000 initiates learning 1002 utilizing knowledge base 1004, communication process 1006, user interface 1008, sensor processing algorithms 1010, and sensor information 1012.

Learning 1002 facilitates change in information stored in knowledge base 1004, specifically the learned knowledge base and online knowledge base components of knowledge base 1004. Communication process 1006 may provide input and data from a variety of sources, such as, without limitation, back office software, the internet, wireless transmitters from other vehicles, and the like. User interface 1008 allows an operator to input data from human observation to update or confirm information in knowledge base 1004. Sensor processing algorithms 1010 receives sensor information 1012 from a sensor system of a vehicle, and processes sensor information 1012 in conjunction with stored data in knowledge base 1004 to identify existing conditions of an operating environment. Learning 1002 also may identify anomalies or changes in the environment that may require alerts or updates. These alerts or updates may be stored in knowledge base 1004 for later use. For example, learning 1002 may identify objects that may be unexpected or undesirable based on knowledge base 1004. For example, without limitation, learning 1002 may identify potholes that need to be repaired, trees that require trimming, improperly parked vehicles, a stolen vehicle, and other suitable objects. This information may be stored in learned knowledge base 806 in FIG. 8. Further, this information may be transmitted to online knowledge base 804 in FIG. 8.

With reference now to FIG. 11, a block diagram of a format in a knowledge base used to select sensors for use in planning paths and obstacle avoidance is depicted in accordance with an illustrative embodiment. This format may be used by path planning module 904 and obstacle detection module 906 in FIG. 9.

The format is depicted in table 1100 illustrating heterogeneous sensor redundancy for localization of the vehicle. Global positioning systems 1102 would likely not have real time kinematic accuracy in a typical street environment due to structures and vegetation. Normal operating conditions 1104 would provide good to poor quality signal reception 1106 because the global positioning system signal reception quality would depend upon the thickness of the tree canopy over the street. In early fall 1108, when some leaves are still on the trees and others are filling the gutter or ditch alongside the road, the canopy thickness may offer good to poor quality signal reception 1110. However, in winter 1112, when trees other than evergreens tend to have little to no leaves, signal reception may be good to very good 1114.

Visible camera images of a curb or street edge 1116 might offer excellent quality images 1118 in normal operating conditions 1104. Other boundaries may be defined by changes in height or changes in ground cover where ground cover includes, but is not limited to, grass, weeds, crop, soil, gravel, sand, asphalt, concrete, brick, wood, plastic, water, snow, ice, and chemicals including paint. However, in early fall 1108 and winter 1112, when leaves or snow obscure curb or street edge visibility, visible camera images would offer unusable quality images 1120 and 1122. Visible camera images 1124 of the area around the vehicle, with an image height of eight feet above the ground, would offer excellent quality images 1126, 1128, and 1130 in most seasons, although weather conditions, such as rain or fog may render the images unusable. Landmarks identified at eight feet above the ground include objects, such as, without limitation, houses, light poles, and tree trunks. This height is typically below tree canopies and above transient objects, such as cars, people, bikes, and the like, and provides a quality zone for static landmarks.

Visible camera images of the street crown 1132 may offer good quality images 1134 in normal operating conditions 1104. The street crown is typically the center of the street pavement, and images of the pavement may be used in pavement pattern matching for vehicle localization. In early fall 1108, when leaves begin to fall and partially obscure the pavement, visible camera images of the street crown 1132 may be good to poor quality images 1136 depending on the amount of leaves on the ground. In winter 1112, the visible camera images of the street crown 1132 may be unusable quality images 1138 due to fresh snow obscuring the pavement.

Lidar images of a curb 1140 using pulses of light may be excellent 1142 for detecting a curb or ground obstacle in normal operating conditions 1104, but may be unusable 1144 when curb visibility is obscured by leaves in early fall 1108 or snow in winter 1112. Lidar detection of the area eight feet above the ground 1146 around the vehicle may be excellent 1148 in normal operating conditions 1104, early fall 1108, and winter 1112, because the landmarks, such as houses and tree trunks, are not obscured by falling leaves or fresh snow. Lidar images of the sky 1150 capture limb patterns above the street for use in limb pattern matching for vehicle localization. Lidar images of the sky 1150 would be unusable due to the canopy 1152 in normal operating conditions 1104, and unusable to poor 1154 in the early fall 1108 when the majority of leaves remain on the limbs. However, lidar images of the sky 1150 may be excellent 1156 in winter 1112 when limbs are bare.

With reference now to FIG. 12, a flowchart illustrating a process for side-following is depicted in accordance with an illustrative embodiment. This process may be executed by path planning module 904 in FIG. 9.

The process begins by receiving user input to engage autonomous mode (step 1202). The user input may be executed by a state machine, such as state machine 500 in FIG. 5, in order to place the vehicle in automated moving state 502. The process identifies following conditions (step 1204) and identifies the position of the leader (step 1206). Follow conditions are stored as part of the side-following process 702 in behavior library 700. Follow conditions may be conditions, such as, without limitation, identifying an authenticated worker in the safe zone around the vehicle, identifying no unauthenticated person in the safe zone around the vehicle, detecting the authenticated worker towards the front of the vehicle, detecting the authenticated worker at a side of the vehicle, detecting that the position of the authenticated worker is changing towards the next location in a planned path, and the like. The leader may be an authenticated worker identified through various means including, without limitation, a radio frequency identification tag located on the person of the authenticated worker, user input by an authenticated worker identifying the worker as a leader, or user input by an authenticated worker identifying another vehicle as a leader.

Next, the process plans a path for the vehicle based on movement of the leader (step 1208) and moves the vehicle along the planned path (step 1210). Path planning module 904 in FIG. 9 plans the path for the vehicle based on movement of the operator detected by a sensor system, such as sensor system 210 in FIG. 2. Sensor system 210 sends sensor information, such as sensor information 918, to sensor processing algorithms 916 in machine controller 900. Path planning module 904 uses the sensor information to move the vehicle along the planned path following the operator. Next, the process determines whether an obstacle is present in the path (step 1212) using an obstacle detection module, such as obstacle detection module 906 in FIG. 9. If an obstacle is present in the path, the process executes avoidance maneuvers to avoid the obstacle (step 1214), then continues to monitor the leader position (step 1216). The avoidance maneuvers may be instructions stored in behavior library 912 in FIG. 9, and executed by obstacle detection module 906 in FIG. 9. If an obstacle is not present in the path, the process continues to monitor the leader position (step 1216). While monitoring the position of the leader, the process determines whether the leader is still at a side of the vehicle (step 1218). The process may determine the position of the leader by using sensors of sensor system 210 in FIG. 2.

If the leader is still at a side of the vehicle, the process continues on the planned path for the vehicle based on movement of the leader (step 1208). If the leader is no longer at a side of the vehicle, the process then determines whether the vehicle should continue following the leader (step 1220). If the process determines that the vehicle should continue following the leader, it returns to the planned path for the vehicle based on movement of the leader (step 1208). However, if the process determines that the vehicle should not continue following the leader, the process stops vehicle movement (step 1222), with the process terminating thereafter.

Figure 13:
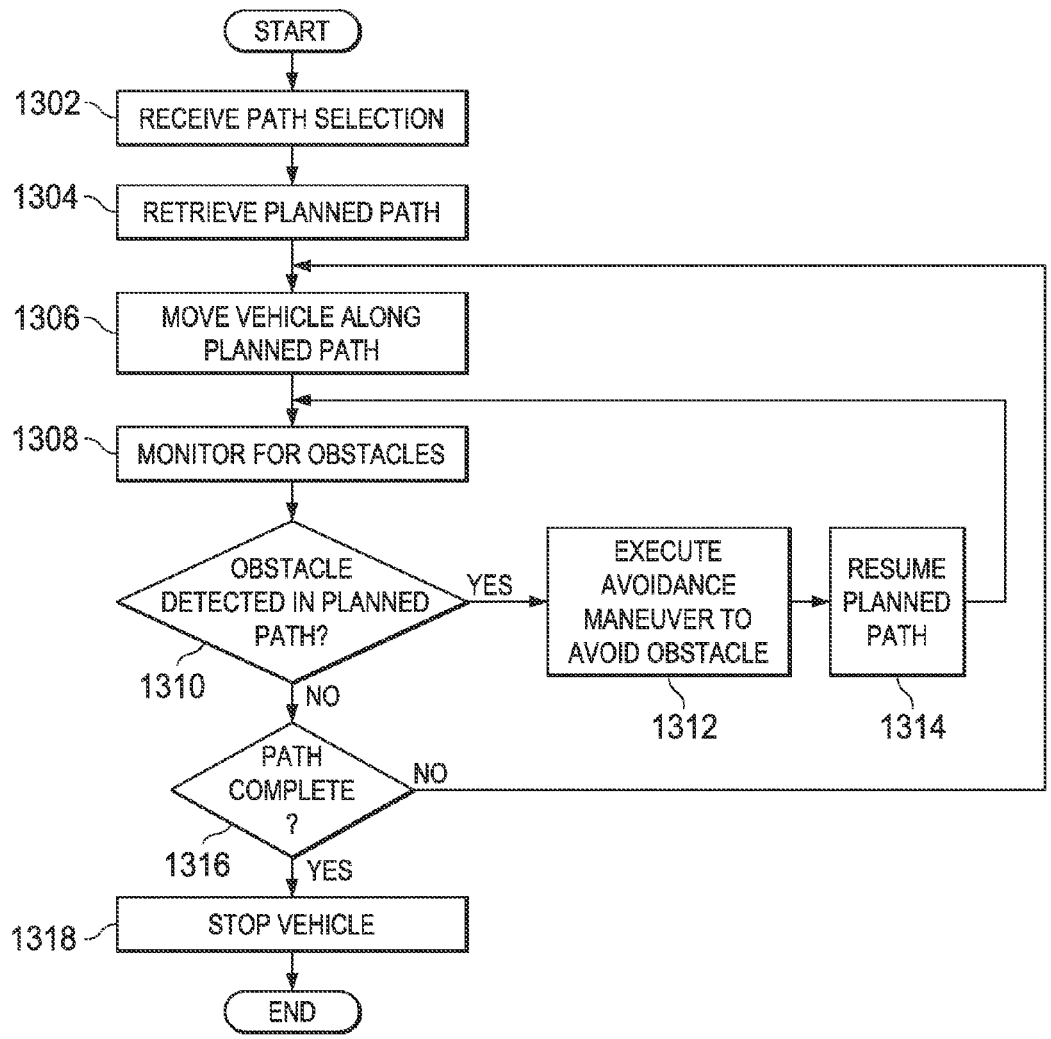
FIG. 13 is a flowchart illustrating a process for side-following in which the planned path may be mapped, taught by driving the path, or a straight path in accordance with an illustrative embodiment.

With reference now to FIG. 13, a flowchart illustrating a process for side-following in which the planned path may be mapped, taught by driving the path, or a straight path is depicted in accordance with an illustrative embodiment. This process may be executed by path planning module 904 in FIG. 9.

The process begins by receiving a path selection (step 1302) and retrieving a planned path (step 1304) based on the path selection. The path selection may be received by user input via user interface 606 in FIG. 6, or by other input received via communications unit 212 in FIG. 2. The planned path is retrieved from knowledge base 608 in FIG. 6. The planned path may be a path generated during a teach and playback mode. For example, in an illustrative embodiment, a path planning module, such as path planning module 904 in FIG. 9, records the location of the vehicle at one or more waypoints received through user input. The waypoints are stored in the knowledge base in association with a path. The path may then be retrieved as part of the playback process of the teach and playback mode.

In another illustrative embodiment, the planned path retrieved may be a straight line or mapped path input via back office software and stored in the knowledge base for future use.

Next, the process moves the vehicle along the planned path (step 1306) and monitors for obstacles (step 1308). The process determines whether an obstacle is detected in the planned path (step 1310). Obstacle detection is performed by an obstacle detection module, such as obstacle detection module 906 in FIG. 9. If an obstacle is detected, the process executes avoidance maneuvers to avoid the obstacle (step 1312), then resumes the planned path (step 1314), and continues to monitor for obstacles (step 1308). If no obstacle is detected, the process determines whether the path is complete (step 1316). If the path is not complete, the process continues to move the vehicle along the planned path (step 1306). If the path is complete, the process stops the vehicle (step 1318), with the process terminating thereafter.

Figure 14:
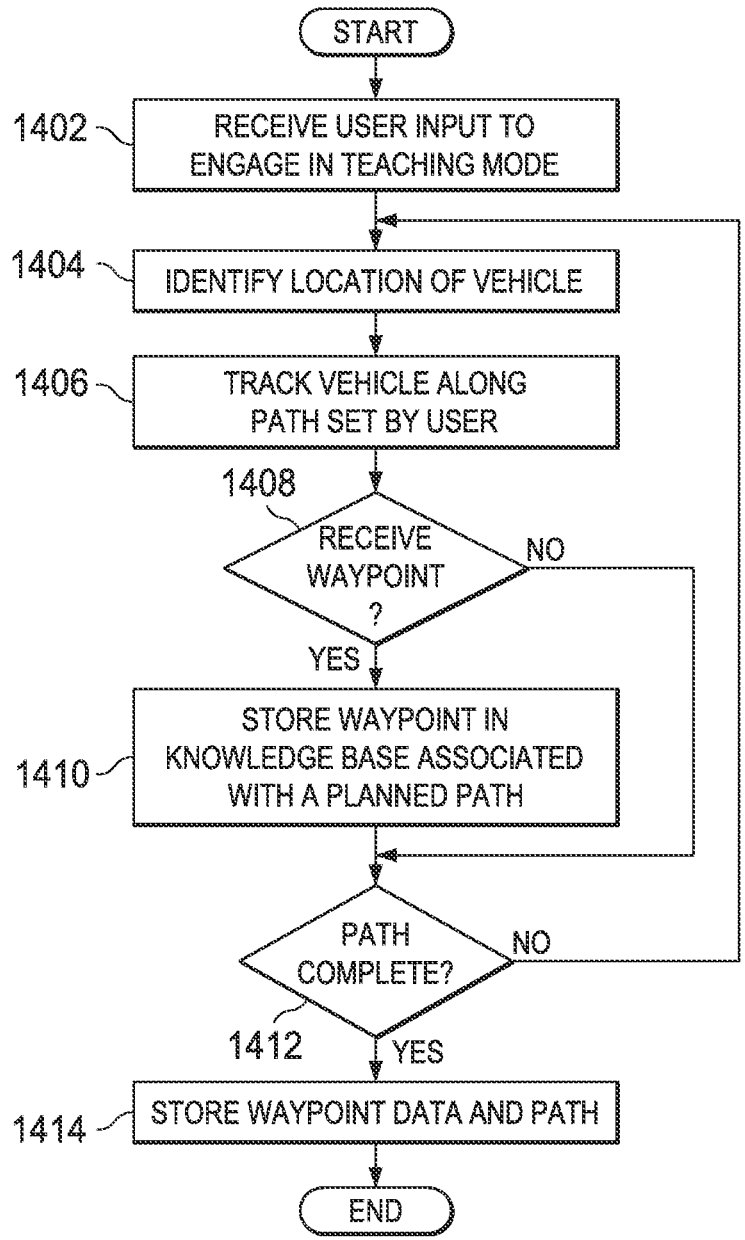
FIG. 14 is a flowchart illustrating a process for teaching an automated vehicle in accordance with an illustrative embodiment.

With reference now to FIG. 14, a flowchart illustrating a process for teaching an automated vehicle is depicted in accordance with an illustrative embodiment. This process may be executed by path planning module 904 in FIG. 9.

The process begins by receiving user input to engage in teaching mode (step 1402). The process identifies the location of the vehicle (step 1404) using a sensor system, such as sensor system 210 in FIG. 2. The sensor system may use, for example, a global positioning system to determine location of the vehicle on a map. Next, the process tracks the vehicle along a path set by the user (step 1406) and determines whether a waypoint is received (step 1408). If a waypoint is received from the user, the process stores the waypoint in the knowledge database associated with the planned path (step 1410). After storing the waypoint, or if no waypoint is received, the process determines whether the path is complete (step 1412). If the path is not complete, the process returns to identify the location of the vehicle (step 1404), and receive further waypoints. If the path is complete, the process stores the waypoint data and the path (step 1414), with the process terminating thereafter.

Figure 15:
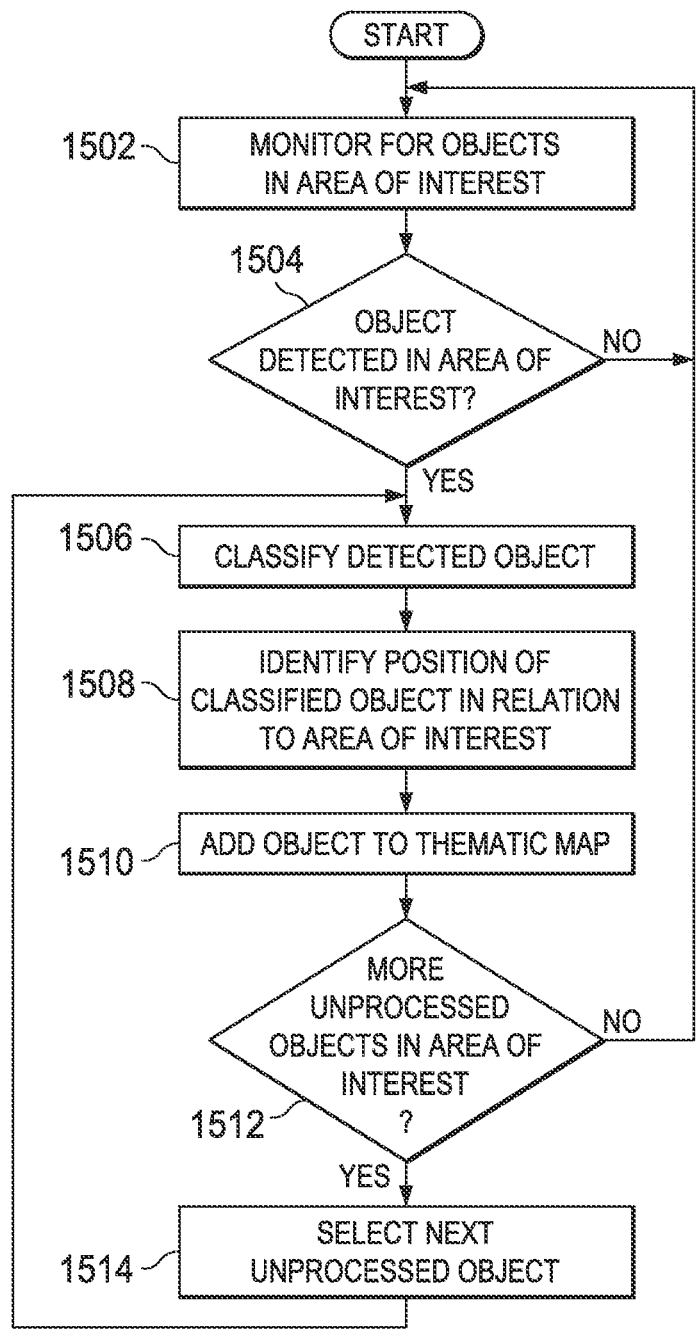
FIG. 15 is a flowchart illustrating a process generating a thematic map of an operating environment in accordance with an illustrative embodiment.

With reference now to FIG. 15, a flowchart illustrating a process for generating a thematic map of an operating environment is depicted in accordance with an illustrative embodiment. This process may be executed by operating environment module 908 in FIG. 9.

The process begins by monitoring for objects in an area of interest (step 1502). An area of interest may be, for example, a work area or a specific planned path. The process determines whether objects are detected in the area of interest (step 1504). If no objects are detected, the process continues to monitor for objects (step 1502). If one or more objects are detected in step 1504, the process classifies the detected objects (step 1506). A sensor processor, such as sensor processing algorithms 916 in FIG. 9, receives sensor data from a sensor system, such as sensor system 210 in FIG. 2, and classifies the sensor data into thematic features by assigning data classifiers.

Next, the process identifies the position of the classified object in relation to the area of interest (step 1508), and adds the classified object to a thematic map (step 1510). The thematic map is generated by operating environment module 908 in FIG. 9, and may be used by a path planning module, such as path planning module 904 in FIG. 9 to determine objects and boundaries for a planned path. The thematic map may also be used by an obstacle detection module, such as obstacle detection module 906 in FIG. 9 to identify and avoid obstacles in a planned path. The process then determines whether more unprocessed objects are in the area of interest (step 1512). If there are more unprocessed objects, the process selects the next unprocessed object (step 1514) and classifies the detected object (step 1506). If there are no more unprocessed objects in step 1512, the process returns to monitor for objects in the area of interest (step 1502). The process may be continuous or may be repeated at selected intervals as the vehicle moves along a planned path.

Figure 16:
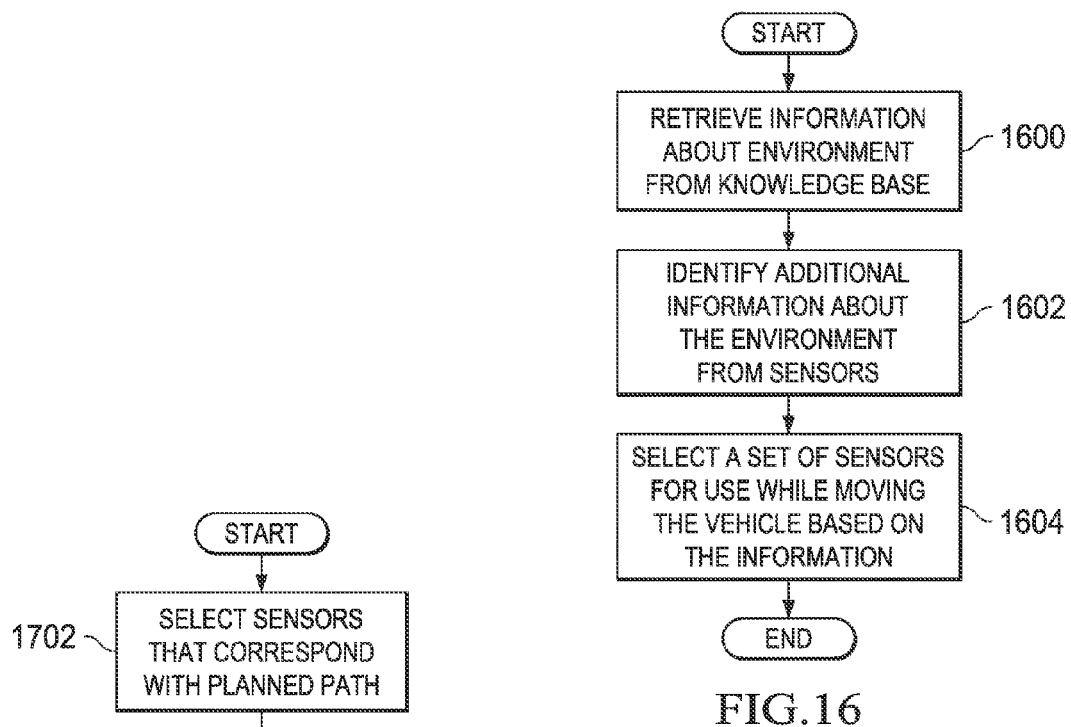
FIG. 16 is a flowchart illustrating a process for sensor selection based on an environment in accordance with an illustrative embodiment.

With reference now to FIG. 16, a flowchart illustrating a process for sensor selection based on the environment is depicted in accordance with an illustrative embodiment. This process may be implemented by sensor processing algorithms 916 in FIG. 9.

The process begins by retrieving information about the environment from the knowledge base (step 1600). The process identifies additional information about the environment from sensors (step 1602) and selects a set of sensors for use while moving the vehicle based on the information (step 1604), with the process terminating thereafter.

Figure 17:
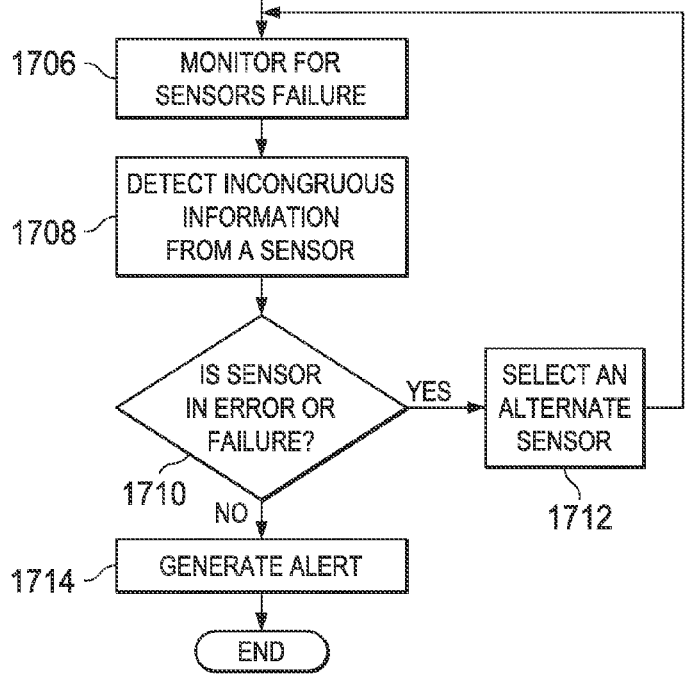
FIG. 17 is a flowchart illustrating a process for sensor transition due to sensor failure in accordance with an illustrative embodiment.

With reference now to FIG. 17, a flowchart illustrating a process for sensor transition due to sensor failure is depicted in accordance with an illustrative embodiment. This process may be implemented by machine controller 202 in FIG. 2.

The process begins by selecting sensors that correspond with the planned path (step 1702). For example, a planned path of a residential street may correspond with a visible camera sensor during summer months when the curb is clearly visible. Next, the process activates the selected sensors (step 1704) and monitors for sensor failure (step 1706). When the process detects incongruous information from a sensor (step 1708), the process determines whether the sensor is in error or failure (step 1710). If the sensor is in error or failure, the process selects an alternate sensor (step 1712), and continues to monitor for sensor failure (step 1706). If the sensor is not in error or failure, the process generates an alert (step 1714), with the process terminating thereafter.

Figure 18:
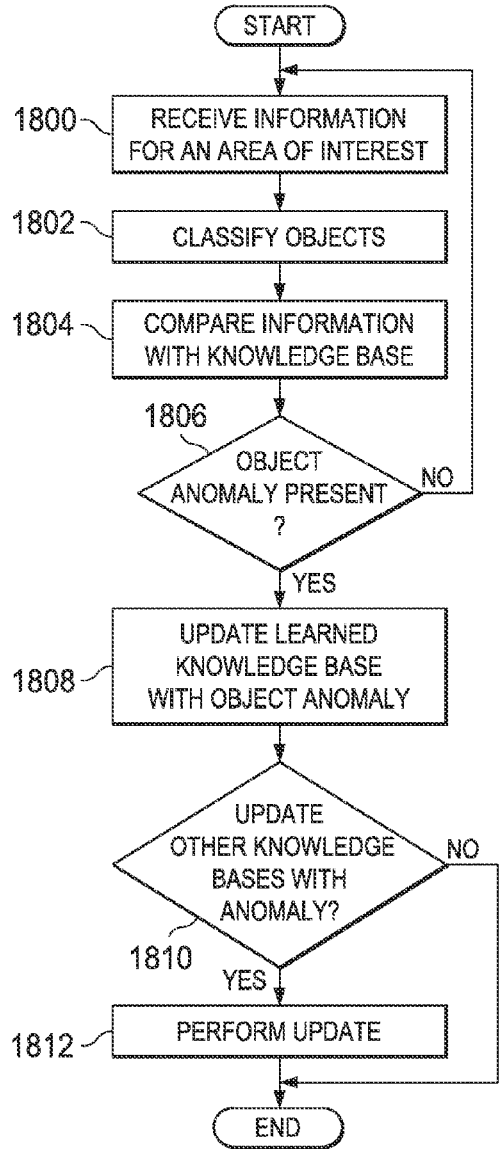
FIG. 18 is a flowchart of the learning process in accordance with an illustrative embodiment.

With reference now to FIG. 18, a flowchart of the learning process is depicted in accordance with an illustrative embodiment. The process illustrated in FIG. 18 may be implemented in a software component, such as learning 1002 in FIG. 10.

The process begins by receiving information for an area of interest (step 1800). This information may be received from a process, such as sensor processing algorithms 1010 in FIG. 10. The process then classifies objects in the area of interest (step 1802). The classification of objects may include, for example, without limitation, identifying the object and attributes for the object. These attributes may be, for example, color, size, dimensions, and other suitable information. The process then compares the information for the classified objects in the area of interest with a knowledge base (step 1804).

A determination is made as to whether an object anomaly is present (step 1806). An object anomaly may be identified using the knowledge base. For example, an a priori knowledge base and/or an online knowledge base may be consulted to determine whether any of the classified objects have attributes that are different enough from the expected attributes. Further, step 1806 also may involve determining whether objects are present in the environment where objects are unexpected or should not be present. For example, step 1806 may identify vehicles that are parked in no parking areas based on information from the knowledge base. As another example, step 1806 may identify potholes, trees that need trimming, stolen vehicles, or other object anomalies of interest. If an object anomaly is not present, the process then returns to step 1800. In these examples, an object anomaly also may be an absence of an object. For example, if a tree is indicated as being present in an online knowledge base and the tree is not found in the location, this fact may be considered an object anomaly.

Otherwise, the process updates the learned knowledge base with the object anomaly (step 1808). The process then determines whether other knowledge bases should be updated with the anomalies (step 1810). This decision may be made based on receiving user input. In step 1810, an operator may be alerted to the presence of an object anomaly and asked whether an update should be made to another knowledge base. In another illustrative embodiment, this determination may be made using a set of rules in the knowledge base to determine whether the update should be made. For example, if a car is parked, an update may be sent to an online knowledge base. In this manner, further processing of this information to handle the improperly parked vehicle may be performed. As yet another example, if the anomaly is a pothole, the process may determine that this information should be sent to the online knowledge base such that the pothole may be identified and marked for repairs.

If other knowledge bases are to be updated with the anomaly, the process then performs the update (step 1812). This update may involve sending the information to the knowledge base. Other processing may occur at the knowledge base to handle the information. This other processing may include updating the knowledge base with the new information or sending messages or alerts indicating that actions may need to be taken, with the process terminating thereafter. The process also terminates directly from step 1810 if updates to other knowledge bases with the anomaly are not needed.

Figure 19:
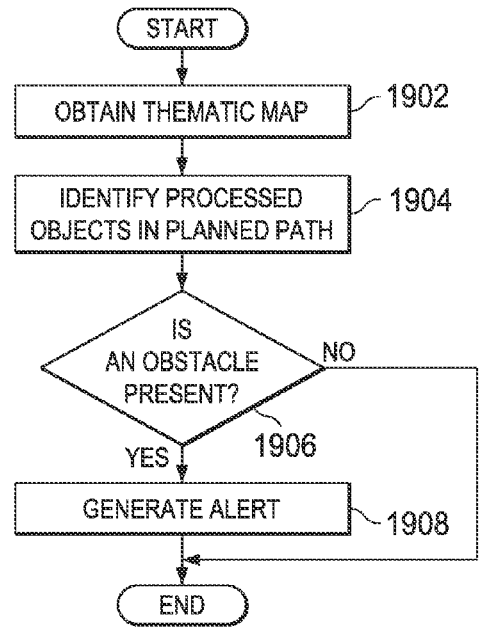
FIG. 19 is a flowchart illustrating a process for obstacle detection in accordance with an illustrative embodiment.

With reference now to FIG. 19, a flowchart illustrating a process for obstacle detection is depicted in accordance with an illustrative embodiment. The process illustrated in FIG. 19 may be implemented in a software component, such as obstacle detection module 906 in FIG. 9.

The process begins by obtaining a thematic map (step 1902). The thematic map may be stored in operating environment module 908 in FIG. 9 or may be continuously generated as operating environment module 908 updates the thematic map with new environmental data. The process identifies processed objects in the planned path (step 1904) that were processed and classified by operating environment module 908 in FIG. 9. Processed objects may include, for example, cars, tree trunks, light poles, curbs, driveways, garage doors, and the like. Next, the process determines whether an obstacle is present (step 1906). For example, the process may determine whether the processed objects are in the planned path of the vehicle or may come into contact with the vehicle as the vehicle moves along the planned path. If an obstacle is present, the process generates an alert (step 1908), with the process terminating thereafter. If an obstacle is not present in step 1906, the process terminates.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The description of the different advantageous embodiments has been presented for purposes of illustration and description, and is not intended to be exhaustive or limited to the embodiments in the form disclosed. Many modifications and variations will be apparent to those of ordinary skill in the art. Further, different embodiments may provide different advantages as compared to other embodiments. The embodiment or embodiments selected are chosen and described in order to best explain the principles of the invention, the practical application, and to enable others of ordinary skill in the art to understand the invention for various embodiments with various modifications as are suited to the particular use contemplated.

What is claimed is:

1. A method for improved vehicle control, the method comprising:
   receiving a power-up command;
   responsive to receiving the power-up command, receiving selection of a side following mode;
   executing a planned path, wherein executing the planned path comprises identifying an operator and distinguishing between the operator and other objects in an environment surrounding the vehicle;
   moving a vehicle along the planned path in a manner that maintains the operator in a position proximate to a side of the vehicle;
   identifying obstacles in the planned path;
   responsive to identifying the obstacles, executing obstacle avoidance maneuvers; and
   responsive to executing obstacle avoidance maneuvers, resuming the planned path.

2. The method of claim 1, wherein identifying the operator comprises receiving video input of the operator walking the planned path.

3. The method of claim 1, wherein identifying the operator comprises detecting an identifying characteristic correlating with a pre-determined list of identifying characteristics for operators.

4. The method of claim 1, further comprising:
receiving user input to override the planned path;
responsive to receiving the user input, suspending the planned path;
executing one or more actions based on the user input; and
resuming the planned path.

5. The method of claim 1, further comprising:
requesting vehicle location information from a high integrity perception system;
receiving the vehicle location information from the high integrity perception system; and
processing the vehicle location information in association with the planned path.

6. The method of claim 1, further comprising:
alerting the environment surrounding the vehicle using audio and visual signals, wherein the audio and visual signals vary dynamically according to one or more factors identified in the environment.

7. The method of claim 1, further comprising:
identifying a boundary to the planned path, wherein the planned path is a ground surface appropriate for vehicle movement; and
maintaining a fixed distance between the vehicle and the boundary identified.

8. The method of claim 7, wherein the boundary is one of a curb and vegetation.

9. A vehicle comprising:
a steering system;
a propulsion system;
a braking system;
a sensor system; and
a machine controller connected to the steering system, the propulsion system, the braking system; and the sensor system, wherein the machine controller identifies movement of an operator using the sensor system and sends commands to the steering system, the propulsion system, and the braking system to move the vehicle in a manner that maintains the operator at a side of the vehicle while the operator is moving.

10. The vehicle of claim 9, wherein the machine controller moves the vehicle in the manner that maintains the operator at the side of the vehicle by identifying a first path for the operator, generating a second path for the vehicle, wherein the second path maintains the operator at the side of the vehicle, and moving the vehicle along the second path.

11. The vehicle of claim 10, wherein the machine controller projects the first path based on direction of movement by the operator.

12. The vehicle of claim 10, wherein the machine controller generates the second path for the vehicle by identifying a boundary to the second path to form an identified boundary, wherein the second path is a ground surface appropriate for movement of the vehicle, and creating the second path to maintain a fixed distance between the vehicle and the identified boundary.

13. The vehicle of claim 12, wherein the boundary is one of a curb and vegetation.

14. The vehicle of claim 10, wherein the machine controller stops the vehicle responsive to detecting an obstacle in the second path.

15. The vehicle of claim 14, wherein the machine controller generates an alert to the operator responsive to the obstacle in the second path being detected.

16. The vehicle of claim 15, wherein the machine controller generates the alert and displays the alert to the operator, wherein the alert is displayed through a user interface.

17. The vehicle of claim 16, wherein the user interface is a display mounted to a side of vehicle and viewable by the operator.

18. The vehicle of claim 15, wherein the machine controller starts the vehicle, responsive to receiving a user input from the operator to move the vehicle around the obstacle, and moves the vehicle around the obstacle based on the user input from the operator.

19. The vehicle of claim 9, wherein the machine controller executes a maneuver to avoid an obstacle responsive to detecting the obstacle in the second path.

20. The vehicle of claim 19, wherein the obstacle is one of a person, a vehicle, and debris in the second path.

21. The vehicle of claim 9, wherein the machine controller further distinguishes the operator from other objects.

22. The vehicle of claim 9, wherein the machine controller further collects data regarding the environment.

23. The vehicle of claim 22, wherein the data comprises a location for at least one of a pothole for repair, a tree requiring trimming, an improperly parked vehicle, and a stolen vehicle.

24. The vehicle of claim 9, wherein the machine controller stops movement of the vehicle in response to a user input from the operator.

25. The vehicle of claim 9, wherein the machine controller starts movement of the vehicle in response to user input from the operator.

26. The vehicle of claim 9, wherein the machine controller classifies objects in an environment around the vehicle.

27. The vehicle of claim 26, wherein the machine controller classifies the objects in the environment around the vehicle using a knowledge base.

28. The vehicle of claim 27, wherein the knowledge base comprises an a priori knowledge base, an online knowledge base, and a learned knowledge base.

29. The vehicle of claim 9, wherein the sensor system comprises a plurality of sensors, and wherein the plurality of sensors comprise at least one of a global positioning system, structured light sensor, two dimensional/three dimensional lidar, dead reckoning, infrared camera, visible light camera, radar, ultrasonic sonar, and radio frequency identification reader.

* * * * *